(12) United States Patent
Kwon et al.

(10) Patent No.: US 8,945,627 B2
(45) Date of Patent: Feb. 3, 2015

(54) MICELLES FOR THE SOLUBILIZATION OF GOSSYPOL

(75) Inventors: Glen S. Kwon, Waunakee, WI (US); Ho-Chul Shin, Madison, WI (US); Hyunah Cho, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/464,737

(22) Filed: May 4, 2012

(65) Prior Publication Data
US 2012/0321715 A1 Dec. 20, 2012

Related U.S. Application Data

(60) Provisional application No. 61/482,864, filed on May 5, 2011.

(51) Int. Cl.
| | | |
|---|---|---|
| *A61K 9/14* | (2006.01) | |
| *A61K 31/11* | (2006.01) | |
| *A01N 43/42* | (2006.01) | |
| *A61K 31/33* | (2006.01) | |
| *A61K 47/02* | (2006.01) | |

(Continued)

(52) U.S. Cl.
CPC .............. *A61K 47/02* (2013.01); *A61K 9/0019* (2013.01); *A61K 9/1075* (2013.01); *A61K 47/10* (2013.01); *A61K 9/12* (2013.01); *Y10S 977/788* (2013.01); *Y10S 977/906* (2013.01)
USPC ........... 424/489; 514/700; 514/449; 514/183; 514/278; 435/375; 977/788; 977/906

(58) Field of Classification Search
USPC .................. 424/489; 514/700, 183, 278, 449; 435/375; 977/788, 906
See application file for complete search history.

(56) References Cited

U.S. PATENT DOCUMENTS

| | | |
|---|---|---|
| 3,740,421 A | 6/1973 | Schmolka |
| 3,925,241 A | 12/1975 | Schmolka |

(Continued)

FOREIGN PATENT DOCUMENTS

| | | |
|---|---|---|
| WO | WO 2009/086324 A1 | 7/2009 |
| WO | WO 2010/059628 A1 | 5/2010 |
| WO | WO 2011/025838 A1 | 3/2011 |

OTHER PUBLICATIONS http://clinicaltrials.gov/archive/NCT00891072/2009_07_09 (available online: Jul. 9, 2009), pp. 1-4.*

(Continued)

*Primary Examiner* — Richard Schnizer
*Assistant Examiner* — Katherine Peebles
(74) *Attorney, Agent, or Firm* — Foley & Lardner, LLP; Joseph P. Meara

(57) ABSTRACT

The invention provides biocompatible micelles loaded with one or more active agents. The micelles can encapsulate anticancer drugs such as gossypol, and combinations of drugs, such as gossypol and paclitaxel, gossypol and 17-AAG, gossypol and cyclopamine, gossypol, paclitaxel, and 17-AAG, and gossypol, paclitaxel, and cyclopamine. The micelle compositions provide effective solubilization of difficult to solubilize drug combinations without the need for additional surfactants that can be toxic to patients. Thus, the invention provides stable and biocompatible drug formulations that improve bioavailability without causing toxicity.

21 Claims, 8 Drawing Sheets gossypol paclitaxel

17-AAG

(51) Int. Cl.
    *A61K 9/00*     (2006.01)
    *A61K 9/107*     (2006.01)
    *A61K 47/10*     (2006.01)
    *A61K 9/12*     (2006.01)

(56) References Cited

U.S. PATENT DOCUMENTS

| | | | |
|---|---|---|---|
| 4,261,989 | A | 4/1981 | Sasaki et al. |
| 4,944,949 | A | 7/1990 | Story et al. |
| 5,399,726 | A | 3/1995 | Holton et al. |
| 5,470,866 | A | 11/1995 | Kingston et al. |
| 5,654,447 | A | 8/1997 | Holton et al. |
| 6,107,332 | A | 8/2000 | Ali et al. |
| 6,118,011 | A | 9/2000 | Mayhew et al. |
| 6,136,961 | A | 10/2000 | Dordick et al. |
| 6,322,805 | B1 | 11/2001 | Kim et al. |
| 7,030,155 | B2 | 4/2006 | Lambert et al. |
| 7,221,562 | B2 | 5/2007 | Song et al. |
| 2003/0008924 | A1 | 1/2003 | Wang et al. |
| 2004/0005351 | A1* | 1/2004 | Kwon et al. ............... 424/450 |
| 2005/0101656 | A1 | 5/2005 | Tian et al. |
| 2005/0256097 | A1 | 11/2005 | Zhong et al. |
| 2006/0019941 | A1 | 1/2006 | Adams et al. |
| 2006/0251710 | A1* | 11/2006 | Kwon et al. ............... 424/450 |
| 2007/0116761 | A1 | 5/2007 | Desai et al. |
| 2007/0122467 | A1* | 5/2007 | Meadows et al. .......... 424/450 |
| 2007/0270396 | A1 | 11/2007 | Santi et al. |
| 2007/0281040 | A1 | 12/2007 | Weichselbaum et al. |
| 2008/0269215 | A1 | 10/2008 | Goldsmith et al. |
| 2009/0123932 | A1 | 5/2009 | Mes-Masson et al. |
| 2009/0281089 | A1 | 11/2009 | Gunzner et al. |
| 2010/0189596 | A1 | 7/2010 | Deng et al. |
| 2010/0267781 | A1 | 10/2010 | Pellechia |
| 2011/0076308 | A1 | 3/2011 | Kwon |

OTHER PUBLICATIONS

Zhai et al. Anticancer research (2008) vol. 28, pp. 2801-2806.*
Nguyen et al. Annals of Thoracic Surgery (2001) vol. 72, pp. 371-379.*
Shafaee et al. Cancer Chemother Pharmacol (2006) vol. 58, pp. 765-770.*
Huh et al. J Controlled Release (2005) vol. 101, pp. 59-68.*
Alexandridis, P., et al. Micellization of Poly(ethylene oxide)-Poly(propylene oxide)-Poly(ethylene oxide) Triblock Copolymers in Aqueous Solutions: Thermodynamics of Copolymer Association. Macromolecules 1994, 27, pp. 2414-2425.
Chou, Ting-Chao. Drug Combination Studies and Their Synergy Quantification Using the Chou-Talalay Method. Cancer Research 2010, 70(2), pp. 440-446.
Horrman, R.M. The three-dimensional question: can clinically relevant tumor drug resistance be measured in vitro? Cancer and Metastasis Reviews 1994, 13, pp. 169-173.

Kunz-Schughart, L.A. The Use of 3-D Cultures for High-Throughput Screening: The Multicellular Spheroid Model. J. Biomol. Screen. 2004, 9, pp. 273-285.
Li, P., Zhao, L. Cosolubilization of non-polar drugs in polysorbate 80 solutions. Int. J. Pharmaceutics 2002, 249, pp. 211-217.
Vogler, M., et al. Bcl-2 inhibitors: small molecules with a big impact on cancer therapy. Cell Death and Differentiation 2009, 16, pp. 360-367.
Zhang, X., et al. pment of amphiphilic diblock copolymers as micellar carriers of taxol. Int. J. Pharmaceutics 1996, 132, pp. 195-206.
Banerji, U., et al., "A pharmacokinetically (PK)-pharmacodynamically (PD) guided phase I trial of the heat shock protein 90 (HSP90) inhibitor 17-allylamino,17-demethoxygeldanamycin (17AAG)," Proc. Am. Soc. Clin. Oncol., 2003, vol. 22, abstract 797.
Banerji, U.,et al., "Pharmacokinetic-Pharmacodynamic Relationships for the Heat Shock Protein 90 Molecular Chaperone Inhibitor 17-Allylamino, 17-Demethoxygeldanamycin in Human Ovarian Cancer Xenograft Models," 2005, Clin Cancer Res 11, pp. 7023-7032.
Baumgrass, R., et al., "Reversible Inhibition of Calcineurin by the Polyphenolic Aldehyde Gossypol," Journal of Biological Chemistry, Dec. 21, 2001, vol. 276, No. 51, pp. 47914-47921.
Fung, A.S., et al., "Concurrent and Sequential Administration of Chemotherapy and the Mammalian Target of Rapamycin Inhibitor Temsirolimus in Human Cancer Cells and Xenografts," Sep. 1, 2009, Clin. Cancer Res., vol. 15, No. 17, pp. 5389-5395.
Gaucher, G., et al., "Block copolymer micelles: preparation, characterization and application in drug delivery," J. Control. Release, Dec. 5, 2005, vol. 109, pp. 169-188.
Ge, J., et al., "Design, synthesis, and biological evaluation of hydroquinone derivatives of 17-amino-17-demethoxygeldanamycin as potent, water-soluble inhibitors of Hsp90," J. Med. Chem, 2006, vol. 49, No. 15, pp. 4606-4615.
Goetz, M., et al., "A phase I trial of 17-Allyl-Amino-Geldanamycin (17-AAG) in patients with advanced cancer," Eur. J. Cancer, Nov. 20, 2002, vol. 38, Supp. 7, pp. S54-S55.
International Preliminary Report on Patentability and Written Opinion for Intl. Pat. Appln. No. PCT/US2012/036635, mailed on Nov. 14, 2013, 7 pp.
International Search Report for Intl. Pat. Appln. No. PCT/US2012/036635, dated Sep. 26, 2012, 4 pp.
Kang, M. H., et al., "Bcl-2 Inhibitors: Targeting Mitochondrial Apoptotic Pathways in Cancer Therapy," Clin. Cancer Res., Feb. 15, 2009, vol. 15, No. 4, p. 1126-1132.
Ready, N., et al., "AT-101 or placebo (P) with docetaxel (D) in second-line NSCLC with gene signature biomarker development," J. Clin. Oncol., May 20, 2009, vol. 27, No. 15S, Abstract 3577, 1 page.
Akers, M.J., "Chapter 41: Parenteral Preparations," Remington: The Science and Practice of Pharmacy, Troy, D.B., Williams & Wilkins, 21st Ed., 2005, pp. 803-849.
Yasugi, K., et al., "Preparation and characterization of polymer micelles from poly(ethylene glycol)-poly(d,l-lactide) block copolymers as potential drug carrier," J. Control. Release, 1999, vol. 62, pp. 89-100.

* cited by examiner gossypol paclitaxel

17-AAG

MICELLES FOR THE SOLUBILIZATION OF GOSSYPOL

RELATED APPLICATIONS

This application claims priority under 35 U.S.C. §119(e) to U.S. Provisional Patent Application No. 61/482,864, filed May 5, 2011, which is incorporated herein by reference.

GOVERNMENT SUPPORT

This invention was made with government support under AI043346 and CA161537 awarded by the National Institutes of Health. The government has certain rights in the invention.

BACKGROUND OF THE INVENTION

As cancer research progresses, it is increasingly evident that single drug formulations provide only limited treatment success. Patients would therefore benefit from the development of suitable combination therapies. One of the most important requirements of combination therapy is a simple and efficacious drug delivery system. Many currently used chemotherapeutics are poorly water soluble, which significantly complicates the process of partnering the chemotherapeutic with a suitable delivery system. Combining two or three drugs in a formulation presents additional challenges in clinical practice because of compatibility and stability issues. Safer and more effective delivery of drug combinations relies on the development of biocompatible delivery systems capable of solubilizing the drug combination without using harsh surfactants or excipients. Stable and biocompatible drug formulations that improve bioavailability without causing toxicity are urgently needed in the field of cancer research and therapy.

One of the fundamental features of cancer is deregulation of apoptosis. Apoptosis occurs following the triggering of cell surface death receptors (the extrinsic pathway) or after the perturbation of mitochondria (the intrinsic pathway). Members of the Bcl-2 family control the integrity of the outer mitochondrial membrane and are therefore important targets for inducing apoptosis via the intrinsic pathway. The resistance of many tumors to chemotherapy is associated with high levels of antiapoptotic Bcl-2 family members. Gossypol has been identified as an effective inhibitor of Bcl-2 proteins, although gossypol has very low aqueous solubility and effective drug delivery systems are needed for its further development as a clinical therapy.

Accordingly, stable and biocompatible drug formulations that improve bioavailability without causing toxicity are needed for improving cancer therapy. An effective drug delivery system for solubilizing Bcl-2 inhibitors, such as gossypol, is also needed. A drug delivery vehicle that can solubilize efficacious drug combinations, preferably without the use of pharmaceutical excipients that result in treatment complications, would significantly advance clinical cancer therapy. An effective combination drug therapy regimen that targets more than one cancer cell growth mechanistic pathway would also significantly aid cancer research and the development of effective clinical therapies.

SUMMARY

The invention provides poloxamer micelles for the solubilization of gossypol; as well as the combinations of gossypol and other important therapeutics. Examples of such combinations include gossypol and paclitaxel; gossypol and 17-AAG; gossypol and cyclopamine; gossypol, paclitaxel, and 17-AAG, and gossypol, paclitaxel, and cyclopamine. The gossypol, paclitaxel, 17-AAG, and cyclopamine can each be exchanged for their analogs and derivatives (their respective 'compounds'), as described below. The invention provides for a safe and simple intravenous delivery of gossypol, as well as the two and three drug combinations, by incorporating the drugs into polymer micelles described herein. Additional aspects of the invention provide the aqueous solubilization of gossypol and the improved solubilization of paclitaxel, 17-AAG, and/or cyclopamine.

The three drug combination can exert its anticancer effects by inhibiting two major cancer survival mechanisms: 1) over-expression of anti-apoptotic proteins and 2) over-expression of heat shock proteins. An advantage of poloxamer 188 is that it is biocompatible and is an FDA approved polymer.

The invention therefore provides micelle compositions that include an aqueous solvent system and drug-encapsulating micelles. The micelles can include a plurality of polymers having an average molecular weight of about 1,000 to about 30,000. The polymers can be, for example, poloxamer polymers or PEG-b-PCL polymers. The polymers can form one or more micelles, and one or more of the micelles encapsulates a drug within their micelle structure, and the drug is not covalently bound to the polymer. The drug can be a gossypol compound, such as one or more of the gossypol compounds described herein. The micelles can optionally include a second or third type of drug compound. The diameter of the micelles can be about 15 nm to about 150 nm.

The invention also provides compositions of the polymers and drugs in the absence of water, where the polymer and drug composition is in the form of a powder. Such powders can be obtained during the process of making micelles, or they can be obtained by, for example, lyophilizing the micelles, for long-term storage.

In one embodiment, the drug can be gossypol or apogossypol, and the poloxamer polymer can be poloxamer 188.

The invention also provides pharmaceutical compositions that include a micelle composition as described herein, where the composition is formulated for intravenous or intraperitoneal administration. The aqueous carrier can be, for example, saline or an aqueous carbohydrate solution. Other components may be optionally included in the composition, such as a buffer or a preservative.

The invention further provides methods for inhibiting the growth of cancer cells. The methods can include contacting the cancer cells with an effective amount of a composition or formulation as described herein that inhibits the growth of the cancer cells. Such inhibition can be partial or complete, and can be in vitro or in vivo.

The invention additionally provides methods of inhibiting the growth of cancer cells and/or killing cancer cells. The methods can include contacting the cells with an effective inhibitory or lethal amount of a composition or formulation as described herein that inhibits the growth of the cancer cells or kills cancer cells.

The invention also provides methods of treating a hyperproliferative disease in a subject by administering to a subject having a hyperproliferative disease a therapeutically effective dose of a composition or formulation as described herein and optionally one or more additional active agents. The methods can optionally be used in combination with radiation, heat, both radiation and heat, and/or other care options.

The invention further provides methods of simultaneously administering two or three drugs to a patient that has, or has been diagnosed with, a cancer that can be treated by the administration of at least one of gossypol, paclitaxel, and 17-AAG. The methods can include administering to a patient that has such a cancer an effective amount of a composition or formulation as described herein; wherein the cancer is thereby treated.

The invention also provides methods of sequentially administering two or three drugs to a patient that has, or has been diagnosed with, cancer that can be treated by administration of at least one of gossypol, paclitaxel, and 17-AAG; comprising administering an effective amount of a gossypol-containing micelle composition comprising as described herein; followed by administering an effective amount of a second composition comprising a drug selected from paclitaxel, 17-AAG, or a combination thereof; and optionally followed by administering an effective amount of a third composition comprising a drug selected from paclitaxel, 17-AAG, or a combination thereof; wherein the cancer is thereby treated.

The various micelle compositions can be formulated into water soluble IV formulations. Examples of these formulations include: (a) a water soluble IV formulation of gossypol enabled by (solubilized in) poloxamer 188 micelles, free or substantially free of toxic organic solvents or toxic surfactants that are often used for IV administration; and (b) a water soluble IV formulation of (i) gossypol and paclitaxel loaded poloxamer 188 micelles, (ii) gossypol and 17-AAG loaded poloxamer 188 micelles, or (iii) gossypol, paclitaxel, and 17-AAG loaded poloxamer 188 micelles; where the formulation exerts additive and/or synergistic anticancer activity against lung cancer cells, for example, non-small cell lung cancer (NSCLC) cells or small cell lung cancer (SCLC) cells.

In another embodiment, the invention provides a pharmaceutical composition comprising an aqueous carrier and a gossypol compound encapsulated in poloxamer micelles. The gossypol compound can be, for example, (−)-gossypol or apogossypol. Additional anticancer agents can be administered concurrently or sequentially. Such agents can include paclitaxel, docetaxel, cisplatin, or combinations thereof, optionally in combination with radiation therapy.

The invention further provides a kit comprising a gossypol compound, a poloxamer polymer, and instructions for administering the gossypol compound to a subject. The kit can also include one or more additional anticancer agents and/or an aqueous carrier. In some embodiments, the gossypol compound is (−)-gossypol or apogossypol, and the additional anticancer agent can be selected from paclitaxel, docetaxel, 17-AAG, cisplatin, and combinations thereof. The invention also provides methods of making the drug loaded poloxamer micelles, for example, using film formation and reconstitution methods, as well as dialysis methods.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

Figure 1:
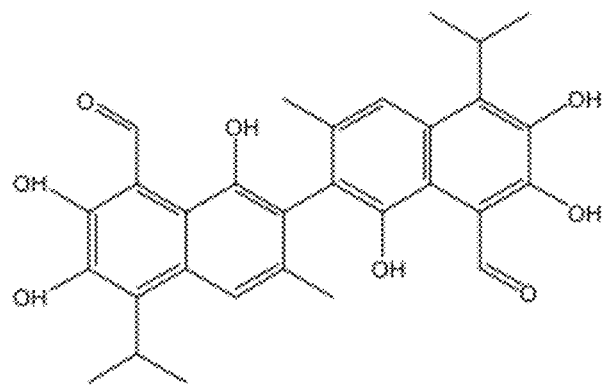
FIG. 1. Chemical structures of gossypol, paclitaxel, and 17-AAG, three difficult to solubilize compounds that can be incorporated into poloxamer micelles.
Figure 1:
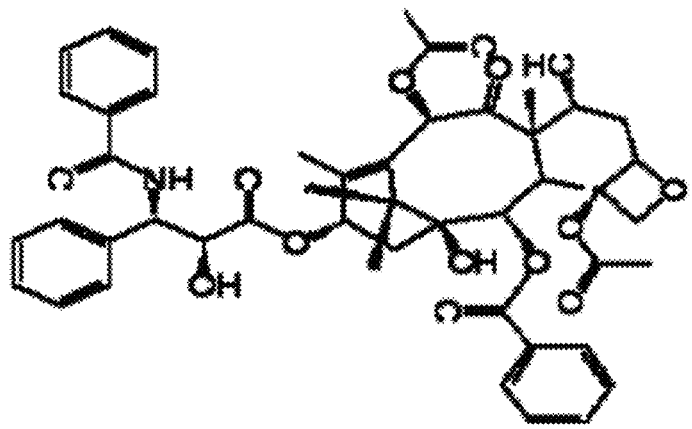
Figure 1:
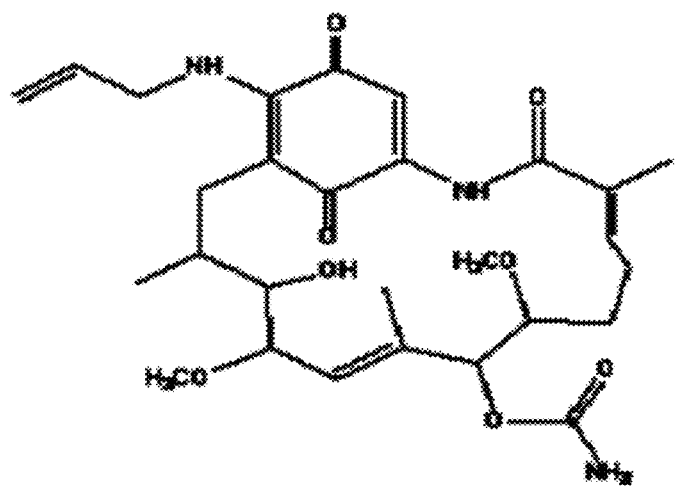

One of the common characteristics of cancer cells is the up-regulation of anti-cell death proteins. Gossypol, a cotton seed extract, targets these proteins and inactivates them. Its enantiomer AT101 (R-(−)-gossypol acetic acid), by itself and in combination with other chemotherapeutics, is currently in clinical trials for the treatment of cancer. Gossypol is notoriously difficult to solubilize and is usually administered orally.

It was surprisingly discovered that gossypol can be solubilized by preparing poloxamer-gossypol micelles that encapsulate the gossypol within the micelles and therefore solubilize the gossypol in an aqueous composition. The dogma in the art of drug solubilization using micelles is that drug solubilization only occurs beyond the critical micelle concentration (CMC). The micelle formation in the presence of gossypol was therefore remarkable because the level of poloxamer 188 used was less than the CMC of the poloxamer. The gossypol surprisingly induced the poloxamer to form micelles at room temperature, thereby resulting in solubilization of the gossypol. It is noteworthy that poloxamer 188 does not form micelles at 25° C. even at very high concentrations (40 mg/mL) (see also Alexandridis et al., *Macromolecules* 1994, 27, 2414-2425), therefore it is extremely significant that poloxamer micelles formed in the presence of gossypol at 25° C. Furthermore, the poloxamer micelles were able to solubilize gossypol in water to a remarkably high concentration (greater than 5 mg/mL).

An additional surprising aspect of the invention is that gossypol further enabled the poloxamer micelles solubilize additional active agents while maintaining micellar stability. For example, the poloxamer 188 micelles can co-solubilize paclitaxel with gossypol (6.53 and 4.65 mg/mL, respectively) without additional poloxamer polymer. This is significant because poloxamer 188 on its own cannot solubilize paclitaxel. Even more remarkably, poloxamer 188 micelles co-solubilize gossypol, paclitaxel, and 17-AAG simultaneously (4.79, 6.28, and 5.65 mg/mL, respectively), while poloxamer 188 micelles can only increase the water solubility of 17-AAG by itself to 0.21 mg/mL. Thus, 17-AAG can be added to the micelles without affecting solubility of the other two drugs.

This is the first report of poloxamer 188 (Pluronic® F68) micelles solubilizing two and three drug combinations of poorly water soluble drugs. Additionally, poloxamer 188 is already approved for use in humans for parenteral drug administration, thus the compositions described herein provide safe and effective vehicles for the delivery of gossypol and gossypol drug combinations, for example, for cancer treatment.

With these novel two and three drug micelle formulations in hand, cell line studies were then carried out. In the cell line studies, the gossypol showed significant toxicity against A549, a non-small lung cancer cell line. Two and three drug combinations were more potent than gossypol alone and showed synergistic activity. Additionally, the two and three drug combinations can not only be solubilized to therapeutically effective levels, but their combinations are synergistic and prevent resistance to the paclitaxel and 17-AAG. For example, the combination of paclitaxel and 17-AAG has synergistic effects; resistance to paclitaxel can be overcome by the presence of 17-AAG, heat shock protein 90 inhibition, and resistance to paclitaxel and 17-AAG can be overcome by the presence of gossypol, a Bcl-2 inhibitor. Thus, these novel drug formulations will provide therapies that are unavailable in any other known formulation.

New formulations for treating cancer are also needed because certain cancers can develop resistance to currently used treatments. Additionally, many patients experience regression of their cancer, which is often fatal. One example of this is ovarian cancer, where the mortality rate is near 55%. In 2002, over 200,000 women were diagnosed with ovarian cancer worldwide. Thus, new therapies are urgently needed.

Ovarian cancer spheroids are significantly resistant to chemotherapy. Therefore, debulking surgery remains a key in ovarian cancer treatment: residual tumors of greater than 2 cm are associated with reduced survival (12-16 months) versus 40-45 months for tumors of less than 2 cm. However, the therapeutic compositions described herein can break apart ovarian cancer spheroids, thus reducing the need for debulking surgery and/or rendering the spheroids more susceptible to chemotherapy. For example, micelles containing a combination of gossypol, cyclopamine, and paclitaxel are very effective at reducing the size of, and breaking apart, ovarian cancer spheroids.

Micelle Polymers and Drug Solubilization.

While many amphiphilic block copolymers can form micelles and can encapsulate certain types of cargo, there is currently no standard for determining which polymers are best suited for encapsulating and solubilizing various types of materials. These determinations must still be made empirically because there is no way to accurately predict which polymers can successfully solubilize a particular material.

Several polymers that form micelles with drugs were surveyed for solubilizing gossypol with numerous failures. The correct set of micellar properties to solubilize gossypol and its drug combinations was not readily apparent. For example, PEG-b-PLA can be used to solubilize several poorly water soluble drugs but PEG-b-PLA does not effectively solubilize gossypol. It is also notable that PEG-b-PLA does not form stable micelles when combined with resveratrol, but PEG-b-PLA does form stable micelles with a paclitaxel-rapamycin-17-AAG drug combination. While the PEG-PPG-PEG triblock polymer poloxamer 188 is useful to solubilize some hydrophobic compounds such as resveratrol, poloxamer 188 was unable to solubilize resveratrol and paclitaxel, or resveratrol and 17-AAG. Thus suitable polymers for solubilizing each drug and drug combination must be determined empirically because no reliable predictive trends exist at this time.

Poloxamer 188 was also unable to solubilize paclitaxel alone to any appreciable level, and only solubilized 17-AAG to a very minor extent. However, when gossypol was added to the combination, all three drugs were solubilized in a stable micelle formulation. Thus poloxamer polymers have been discovered as a useful platform for solubilizing new drug combinations.

Cyclopamine is an important Hedgehog pathway inhibitor that is difficult to solubilize in aqueous compositions. Cyclopamine cannot be solubilized to any practical levels in poloxamer polymers or PEG-b-PCL polymers. However, when incorporated into poloxamer or PEG-b-PCL micelles in the presence of gossypol, significant amounts of cyclopamine can be solubilized, for example, on the order of more than 5 mg/mL. Additionally, at room temperature (~23° C.), poloxamer 188 does not form micelles; however it was found that the presence of gossypol induces micelle formation of the poloxamer polymers, even at room temperature. Finally, even the versatile PEG-b-PLA polymer is ineffective at solubilizing the combination of cyclopamine and gossypol. On the other hand, both cyclopamine and gossypol are efficiently incorporated into micelles by using PEG-b-PCL, which micelles provide a relatively high loading efficiency and even particle size distributions.

The term "poloxamer" refers to a nonionic triblock copolymer composed of a central hydrophobic chain of polyoxypropylene (poly(propylene oxide) (PPO), alternatively referred to as poly(propylene glycol) (PPG)) flanked by two hydrophilic chains of polyoxyethylene (poly(ethylene oxide) (PEO), alternatively referred to as poly(ethylene glycol) (PEG)). The structure of the poloxamer ABC block copolymer can be represented as PEG-PPO-PEG or by the formula:

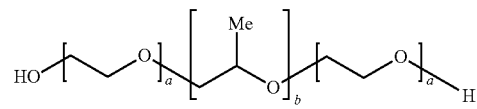

wherein each a is an integer such that the sum of the polyoxyethylene blocks has a total average molecular weight of about 440 to about 16,000 (i.e., where the sum of a units is about 10 to about 360 and each a value can be independently about 5 to about 350); and b is an integer such that the polyoxypropylene block has a molecular weight of about 1,500 to about 5,000 (i.e., where b is about 25 to about 85). In various embodiments, the polyoxyethylene blocks can constitute about 10 wt. % to about 90 wt. % of the copolymer, or about 50 wt. % to about 90 wt. % of the copolymer, and the total average molecular weight of the poloxamer can be about 2,000 to about 21,000.

The lengths of the polymer "a" and "b" blocks can be customized, therefore many different poloxamers can be prepared. For the generic term "poloxamer", these copolymers are commonly named with the letter "P" (for poloxamer) followed by three digits, the first two digits×100 provides the approximate molecular mass of the polyoxypropylene core, and the last digit×10 provides the percentage polyoxyethylene content (e.g., P407=a poloxamer with a polyoxypropylene molecular mass of 4,000 g/mol and a 70% polyoxyethylene content; corresponding to Pluronic® F127). For the Pluronic® tradename, coding of these copolymers starts with a letter to define its physical form at room temperature (L=liquid, P=paste, F=flake (solid)) followed by two or three digits. The first digit (or first two digits in a three-digit number) in the numerical designation, multiplied by 300, indicates the approximate molecular weight of the polyoxypropylene block; and the last digit×10 gives the percentage polyoxyethylene content (e.g., Pluronic L61=a poloxamer with a polyoxypropylene molecular mass of 1,800 g/mol and a 10% polyoxyethylene content). In the example given, poloxamer 181 (P181)=Pluronic L61.

Poloxamers are biocompatible polymers, and poloxamer 188 is FDA approved for use in humans for IV drug administration. Poloxamers can be obtained from, for example, BASF Corporation. Various poloxamers and their preparation are described by U.S. Pat. No. 3,740,421 (Schmolka), and references cited therein. The terminal PEG blocks of the poloxamer can terminate in hydroxyl groups as illustrated above, or one or both of terminal PEG blocks can terminate with alkyl groups, such as methyl groups (e.g., methoxy ethers) or any suitable protecting, capping, or blocking groups.

The poloxamer micelles can be prepared using poloxamer polymers of a variety of different block sizes and in a variety of ratios (e.g., total PEG:PPG of about 1:10 to about 10:1, or any integer ratio within said range). For example, molecular weights ($M_n$) of each of the blocks of the PEG-PPG-PEG polymers can individually be about 0.5K, about 1K, about 2K, about 3K, about 4K, about 5K, about 6K, about 7K, about 8K, about 10K, about 12K, about 15K, and/or a range between any two of the preceding values. When the poloxamers form micelles with drugs, the drug-to-polymer ratio can be about 1:20 to about 10:1, or any integer ratio within such range. Specific examples of suitable drug-polymer ratios include, but are not limited to, about 1:1; about 1:0.5; about 1:0.25; about 1:2.5; about 1:5; about 1:7.5; and/or about 1:10, for each drug individually or for the drugs in combination. It is generally preferable for the mass of the PEG blocks to have a greater total mass than the mass of the PPG block. As the ratio of PPG:PEG increases, the poloxamers lose water solubility and the CMC of the resulting micelles decreases.

One suitable poloxamer polymer is a poloxamer 188 (Pluronic L61). Another suitable poloxamer polymer can be poloxamer 407 (Pluronic F127). Use of poloxamers resulted in unexpectedly high levels of drug loading in micelles formed from them. For example, when a polymer-drug film method was employed, drug loading of about 5.5 mg/mL of gossypol in poloxamer 188 was achieved when the film was reconstituted in warm water.

In other embodiments, the polymer used to prepare the micelles can be the amphiphilic block copolymer polyethylene glycol-b-polycaprolactone (PEG-b-PCL). The hydrophobic PCL block can have a molecular weight of about 1,000 to about 30,000, often about 5,000 to about 20,000, about 8,000 to about 12,000, or about 10,000. The hydrophilic PEG block can have a molecular weight of about 550 to about 20,000, often about 1,000 to about 10,000, about 4,000 to about 6,000, or about 5,000. The PEG-b-PCL polymer can terminate in hydroxyl groups, ($C_1$-$C_{12}$)alkyl groups such as a methyl groups, or typically, one hydroxyl and one alkyl. An example of a useful PEG-b-PCL polymer is:

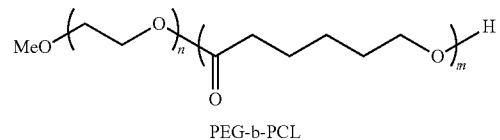

PEG-b-PCL where n is about 50 to about 150, and m is about 50 to about 150. In some embodiments, n can be about 80 to about 130 and m can be about 60 to about 120, n can be about 110 to about 120 and m can be about 70 to about 100, or n can be about 113 and m can be about 88.

Micelle Preparation.

Amphiphilic single chains of amphiphilic polymers dissolved in a solvent in an amount above the critical micelle concentration (CMC) aggregate into a micelle, a core-coronal structure with a hydrophobic interior or core, and hydrophilic exterior or shell. Drug loaded poloxamer micelles readily form in aqueous environments with certain types of therapeutic agents as described herein, where the drug is located at the core of the micelle and not in the corona.

Poloxamer micelles can be prepared as described below and as in the Examples. For example, Preparatory Procedure B provides one specific method for preparing a gossypol, paclitaxel, and 17-AAG micelle formulation. This procedure is merely illustrative for one embodiment, and the technique and amounts of reagents can be varied according to the desired scale of preparation, as would be readily recognized by one skilled in the art.

Preparatory Procedure A:

Simple Equilibrium. In one embodiment, micelle preparation can be carried out as follows. Poloxamer 188 and one, two or three anticancer drugs of interest are dissolved in a suitable water miscible solvent, such as acetonitrile, acetone, or dimethylacetamide, with optional mixing and/or sonication. The solvent is then removed, for example, under reduced pressure, to provide a polymer-drug thin film. Water is added to the polymer-drug film, resulting in spontaneous micelle formation. Warm water (approximately 50° C. to about 70° C.) can also be used, followed by allowing the mixture to cool after spontaneous micelle formation. The drug encapsulating polymeric micelles form upon addition of the water. The micelles can then be isolated, for example, by filtration. See FIG. 2.

Preparatory Procedure B:

Simple Equilibrium. In one embodiment, 21 mg of poloxamer 188, and 2 mg each of gossypol, paclitaxel, and 17-AAG are dissolved in 1-3 mL of acetone. The mixture is mixed for five minutes. The solvent is then removed by rotoevaporation at approximately 60° C. to provide a film. Hot (~60° C.) deionized water is added to the film and the solution is allowed to cool to room temperature (~23° C.). The solution is then centrifuged to remove any sediment in a 1.5 mL microtube, at 13,200 rpm for 1 minute. The supernatant is collected and filtered through a 0.45 μm nylon filter. The isolated micelles can then be stored for extended periods of time at 4° C.

Preparatory Procedure C:

Dialysis. In another embodiment, the micelles can be loaded and formed by the following dialysis procedure. Poloxamer 188 and two or three drugs of the desired ratio (e.g., varying from 1:1:20 to 1:20:1 to 20:1:1 of drugs, respectively) are dissolved in a water miscible solvent, such as dimethylacetamide, acetonitrile, or acetone. The mixture is then added to an aqueous solution, such as a 0.9% saline, in a 3500 MWCO tubing (Spectra/Por®) dialysis bag, whereupon micelles form upon solvent exchange, incorporating the drugs. The micelle mixture can then be centrifuged (e.g., at ~16,000 rpm for 5 minutes) to remove precipitate (unincorporated drug). The supernatant can then be nanofiltered and analyzed, for example, using RP-HPLC (e.g., with UV and RI detection modes; see the techniques described by Yasugi et al., *J. Control. Release*, 1999, 62, 99-100).

Preparatory methods can also include the use of oil-in-water emulsions, solution casting, and/or freeze-drying (lyophilization). Other procedures that can be used include those described by Gaucher et al., *J. Controlled Release*, 109 (2005) 169-188. Once prepared, the micelle-drug composition can be stored for extended periods of time under refrigeration, preferably at a temperature below about 5° C. Temperatures between about –20° C. and about 4° C. have been found to be suitable conditions for the long-term storage of most micelle-drug compositions. Use of brown glass vials or other opaque containers to protect the micelle-drug composition from light can further extend effective lifetimes of the compositions. The micelle-drug compositions can also be freeze-dried into a solid formulation, which can then be reconstituted with an aqueous vehicle prior to use.

Active Agents/Drugs for Poloxamer Micelles.

A variety of active agents can be encapsulated in the poloxamer micelles described herein on account of the remarkable discovery that gossypol facilitates the formation and increases the stability of poloxamer micelles. Other compounds such as resveratrol were able to be solubilized with poloxamer 188 but the resveratrol poloxamer 188 micelles were unstable when other active agents were introduced. Surprisingly, the inclusion of gossypol in the micelle formulation enabled the additional inclusion of one or two additional active agents, such as a paclitaxel compound or a 17-AAG compound, in nearly additive fashion without additional poloxamer.

Gossypol Compounds.

Gossypol is a natural, yellow pigment that can be extracted from the cotton plant (genus *Gossypium*). Gossypol is a phenolic aldehyde that can permeate cells and act as an inhibitor for several dehydrogenase enzymes. Its chemical structure is illustrated in FIG. 1. Gossypol can trigger apoptosis and can act as a co-solvent in 2-in-1 and 3-in-1 micelle formulations. Gossypol can also change cancer cell properties to render them more susceptible to other chemotherapeutic drugs, such as those described herein.

Gossypol is an effective pro-apoptotic agent that inhibits anti-apoptotic Bcl-2 proteins (Bcl-2, Bcl-$X_L$, and Mcl-1). Bcl-2 overexpression is one of mechanisms that is often resistant to chemotherapeutic drugs. Gossypol and its (−) enantiomer (AT101) are currently in clinical trials for the treatment of cancer (Kang, M. H.; Reynolds, C. P.; *Clin. Cancer Res.* 2009, 15, 1126). However, gossypol has a very low aqueous solubility and requires a drug delivery system for solubilization for cancer treatment via the intravenous (IV) route. Nevertheless, there is keen interest in evaluating gossypol as a chemotherapeutic, particularly in the interest of finding synergistic antitumor responses (Ready, N.; Potti, N.; Karaseva, S.; et al. *J. Clin. Oncol.* 2009, 27(15s), abstract 2010).

In the various embodiments described herein, the gossypol can be a racemic mixture, a specific enantiomer, or a combination thereof (i.e., (+/−)-gossypol; (−)-gossypol; (+)-gossypol; or a combination thereof). The gossypol can also be exchanged for various gossypol derivatives or family members ("gossypol compounds"), such as (+/−)-gossypolone; (−)-gossypolone; (+)-gossypolone; (+/−)-gossypol acetic acid; (−)-gossypol acetic acid; (+)-gossypol acetic acid; (+/−)-ethyl gossypol; (−)-ethyl gossypol; (+)-ethyl gossypol; (+/−)-hemigossypolone; (−)-hemigossypolone; (+)-hemigossypolone; (+/−)-apogossypol; (−)-apogossypol; (+)-apogossypol; (+/−)-apogossypol acetic acid; (−)-apogossypol acetic acid; (+)-apogossypol acetic acid; (+/−)-ethyl apogossypol; (−)-ethyl apogossypol; (+)-ethyl apogossypol; or a combination thereof. Other gossypol compounds are described by, for example, U.S. Patent Publication No. 2010/0267781 (Pellechia).

Paclitaxel Compounds.

Paclitaxel is a mitotic inhibitor and known chemotherapeutic agent, the structure of which is illustrated in FIG. 1. Paclitaxel can trigger apoptosis and inhibit mitotic spindle assembly and cell division. Paclitaxel derivatives or analogs may be exchanged with paclitaxel in the formulations herein. Such derivatives and analogs include docetaxel, 7-hexanoyltaxol (QP2), 3'-desphenyl-3'-(4-ntirophenyl)-N-dibenzoyl-N-(t-butoxycarbonyl)-10-deacetyltaxol, and other known paclitaxel derivatives. Several paclitaxel derivatives are known in the art and are disclosed in, for example, U.S. Pat. No. 5,399,726 (Holton et al.); U.S. Pat. No. 5,470,866 (Kingston et al.); U.S. Pat. No. 5,654,447 (Holton et al.); U.S. Pat. No. 6,107,332 (Ali et al.); U.S. Pat. No. 6,118,011 (Mayhew et al.); and U.S. Pat. No. 6,136,961 (Dordick et al.).

17-AAG Compounds.

Geldanamycin is a natural product inhibitor of Heat Shock Protein 90 (Hsp90), obtainable by culturing *Streptomyces hygroscopicus* var. *geldanus* NRRL 3602. Hsp90 is an important target for cancer therapy due to its key role in regulating proteins that are involved in tumor cell proliferation. It was discovered that geldanamycin, a benzoquinone ansamycin antibiotic, strongly binds to the ATP/ADP binding pocket of Hsp90, interfering with the survival and growth of a diverse family of tumors, including HER-2/erbB-2 overexpressing, paclitaxel resistant breast cancers. Clinical development of geldanamycin has been hampered by its poor solubility and severe hepatotoxicity (Ge et al., *J. Med. Chem.* 49(15) (2006) 4606-4615).

The geldanamycin analogues 17-allylamino-17-demethoxygeldanamycin (17-AAG; tanespimycin, FIG. 1) and 17-dimethylamino-ethylamino-17-demethoxygeldanamycin (17-DMAG, alvespimycin) were developed in part to improve the water solubility of geldanamycin. These compounds can be used in place of or in addition to the 17-AAG of the micelles described herein. Additional 17-AAG compounds include 17-hydroxy-ethylamino-17-demethoxygeldanamycin, 17-amionoethyl-hexonate-17-demethoxygeldanamycin, 17-amionoethyl-bromohexonate-17-demethoxygeldanamycin, 17-aminoethyl-dodeconate-17-demethoxygeldanamycin, 17-aminoethyl-bromododeconate-17-demethoxygeldanamycin, 17-amionoethyl-palmitate-17-demethoxygeldanamycin, 17-aminoethyl-bromopalmitate-17-demethoxygeldanamycin, 17-amiono-hexyldecyl-17-demethoxygeldanamycin, which are described by U.S. Patent Publication No. 2006/0251710 (Kwon et al.). Other analogs include the compounds described in U.S. Patent Publication Nos. 2005/0101656 (Tian et al.), 2007/0270396 (Santi et al.), and 2006/0019941 (Adams et al.). Each of these compounds is considered a 17-AAG compound, as used herein, which can be solubilized by poloxamer polymers when combined with a gossypol compound.

The compound 17-AAG is also a promising heat shock protein 90 inhibitor currently undergoing clinical trials for the treatment of cancer. Despite its selective mechanism of action on cancer cells, 17-AAG faces challenging issues due to its poor aqueous solubility. Suitable water solubility is of particular importance for parenteral administration. The water solubility of 17-AAG is only about 0.1 mg/mL at neutral pH, making it difficult to administer in a safe and effective manner. Attempts have been made to address the solubility issue but each formulation was accompanied by its own drawbacks, such as the use of DMSO, ethanol, or various undesirable surfactants.

Current 17-AAG compositions require formulation with Cremophor® EL (CrEL), DMSO, and/or ethanol (see U.S. Application Publication No. 2005/0256097 (Zhong et al.)). The use of CrEL is undesirable from a patient tolerability standpoint because CrEL is known to induce hypersensitivity reactions and anaphylaxis, and requires patient treatment with antihistamines and steroids before administration. Accordingly, safer and more effective delivery of 17-AAG compounds relies on the development of biocompatible delivery systems capable of solubilizing the drug without the use of harsh surfactants, such as the micelle formulations described herein.

Cyclopamine.

Figure 5:
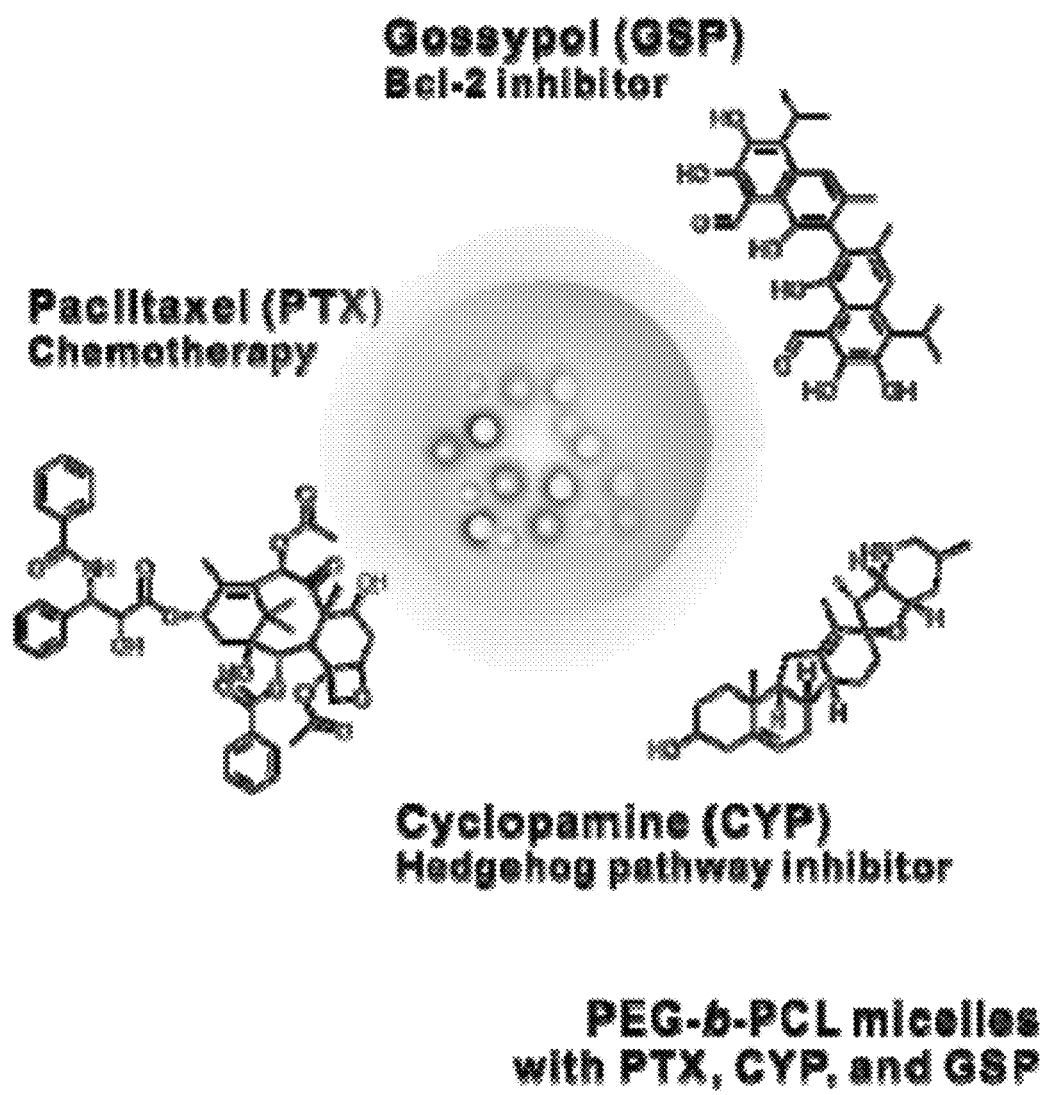
FIG. 5. Three-in-one polymeric micelles carrying paclitaxel, cyclopamine and gossypol. In some embodiments, the polymer can be PEG-b-PCL; in other embodiments, the polymer can be a poloxamer such as poloxamer 188.

Cyclopamine (11-deoxojervine) is a naturally occurring steroid that belongs to the jerveratrum alkaloids, the structure of which is illustrated in FIG. 5. Cyclopamine is a Hedgehog pathway inhibitor that can kill stem-like cancer cells. Cyclopamine is a direct inhibitor of Smoothened, a G protein-coupled receptor protein. Cyclopamine can be useful for treating cancers such as ovarian cancer, pancreatic cancer, and basal cell carcinoma. Other cyclopamine compounds can be used in the micelles described herein in place of cyclopamine, such as those compounds described in U.S. Patent Publication Nos. 2008/0269215 (Goldsmith et al.) and 2009/0281089 (Gunzner et al.).

Combination Drug Therapy.

Combination drug therapy is becoming increasingly important for the treatment of cancer. Researchers are interested in the combination of chemotherapy and signal transduction inhibitors, as well as the combination of different signal transduction inhibitors. Combination cancer therapy is desirable for patients because of various benefits over monotherapy, including slower/less development of drug resistance and synergistic cancer cell-killing effects.

The importance of multi-drug micelles is underscored by the shift in chemotherapy practices to combination drug therapy. This shift has been hampered by the differing solubilities of the therapeutics and different modes of delivery. Combining two or three drugs is often problematic in clinical practice because of solubility, compatibility and stability issues.

In murine tumor models and in early clinical trials, paclitaxel, a chemotherapeutic, has been shown to act synergistically with 17-AAG, a signal transduction inhibitor. However, paclitaxel and 17-AAG are difficult to solubilize, thus effective drug delivery systems are needed for clinical development of drug combination therapy.

Each of gossypol, paclitaxel, and 17-AAG are poorly water-soluble, requiring specialized vehicles for drug solubilization, administration, and delivery. These current drug vehicles also have to be infused separately into patients via sequential drug administration in a single catheter line, increasing time of administration, or via concurrent drug administration in multiple catheter lines, raising risks of infection and adverse drug interactions. Existing vehicles for drug solubilization often include toxic components, such as CrEL. However, the polymeric micelles described herein, prepared from biocompatible poloxamers, can dramatically increase the water solubility of gossypol, paclitaxel, and 17-AAG together in the same nano-sized aqueous vehicle (e.g., a poloxamer micelle composition). These nano-formulations offer a new approach for the delivery of a triple drug combination of gossypol, paclitaxel, and 17-AAG for the inhibition of cancer cell growth and for the treatment of cancer.

The multidrug compositions described herein provide significant advantages to other treatments because lower amounts of one drug can be administered with equivalent or enhanced effect, while also, for example, inhibiting heat shock protein 90 and anti-apoptotic proteins. The drug combination formulations can be provided by preparing either simply mixed micelle formulations (wherein each single micelle contains only one type of active agent, and micelles containing different active agents are combined in one formulation) or co-encapsulated micelle formulations (wherein a micelle contains two or three different active agents).

Accordingly, one, two, and three drug combination formulation of gossypol, paclitaxel and 17-AAG can be prepared, where the drugs are encapsulated within micelles. The micelles can be formulated in aqueous solutions for administering concurrently or sequentially to a patient. In one embodiment, all three drugs can be loaded into micelles at substantially the same level in the same manner as they can be loaded in a single drug micelle formulation. The three-drug micelles were highly stable and remained soluble for more than 24 hours at room temperature (~23° C.), and they showed significant cytotoxicity against cancer cell lines, such as the A549 non-small cell lung cancer (NSCLC) cell line.

One embodiment of the invention provides a single combined formulation that that relies on the unique ability of gossypol to facilitate the solubilization of paclitaxel and 17-AAG in individual poloxamer micelles. An approach with sequentially administered poloxamer micelle drug-encapsulated formulations (where each micelle encapsulates a different drug) can also be used. In one embodiment, the invention provides a single non-toxic formulation carrying multiple anti-cancer drugs. Such formulations are significant improvements over currently used formulations that use toxic excipients such as Cremophor EL, DMSO, and ethanol. The toxicity of excipients becomes even more critical when two- and three-drug cocktails are being administered to a patient, thus the micelles lacking such excipients provide significant advantages for therapeutic applications.

Another embodiment of the invention provides concurrent combination therapy using polymeric micelles carrying three potent therapeutic agents: gossypol, cyclopamine, and paclitaxel. This combination can maximize efficacy and reduce drug resistance by solubilizing the highly hydrophobic drugs in an aqueous solution, minimizing IV injection volume and achieving a highly synergistic cancer cell-killing efficiency. Poly(ethylene glycol)-block-poly(ε-caprolactone) (PEG-b-PCL) assembles into nanoparticles (micelles) that take up a chemotherapeutic agent (paclitaxel), a Hedgehog pathway inhibitor (cyclopamine), and a Bcl-2 inhibitor (gossypol).

Paclitaxel and cyclopamine could not be efficiently loaded in separate individual micelles (<1 mg/mL), but significant amount of both drugs could be loaded (>6 mg/mL) in 3-in-1 micelles when incorporated with gossypol (See Example 2 below). These three-in-one micelles also showed gradual in vitro release kinetics of the three drugs over time.

Various Embodiments of the Invention

The drugs and drug combinations described herein can be encapsulated within poloxamer micelles, which can then be formulated for administration to a subject, such as a human patient in need of therapy for the treatment of cancer. An effective amount of the encapsulated drugs can be administered to a patient, for example, to treat the cancer or inhibit its progression. In some embodiments, the drug combinations include a gossypol compound and any one or two of a paclitaxel compound and a 17-AAG compound (e.g., a suitable and effective analog or derivative of gossypol, paclitaxel, and/or 17-AAG). For example, in certain embodiments, the paclitaxel can be replaced by a similar or equivalent amount of docetaxel. In some embodiments, gossypol can be replaced by a similar or equivalent amount of apogossypol. Likewise, 17-AAG can be replaced by a similar or equivalent amount of 17-DMAG, geldanamycin, or a derivative thereof (such as a compounds described in U.S. Pat. No. 4,261,989 (Sasaki et al.), incorporated herein by reference).

In one embodiment, the invention provides poloxamer micelles loaded with gossypol. In another embodiment, the invention provides poloxamer micelles loaded with gossypol and paclitaxel. In another embodiment, the invention provides poloxamer micelles loaded with gossypol and 17-AAG. In a further embodiment, the invention provides poloxamer micelles filled with gossypol, paclitaxel, and 17-AAG. When administered, the drugs of the micelle formulations can exert synergistic anti-cancer activity. The cancer cell inhibition, killing, or otherwise anti-cancer effect can be achieved using lower doses of the individual drugs than when the drugs are administered without micelles, for example, by oral administration or by use of various excipients.

Preparation of the formulations can be carried out on a large scale. The micelles can be readily sterilized due to the small size of the micelles (15-150 nm). The aqueous micelle formulation makes the drug administration easy because it can be administered intravenously as an aqueous vehicle, and the poloxamers have low toxicity due to their biocompatibility. The formulations can also avoid the noxious vehicles that are required in the clinic for the individual drugs.

Most hydrophobic drugs such as gossypol, paclitaxel, and 17-AAG have a water solubility on the order of micrograms (μg) per mL. The unique combination of these drugs encapsulated in poloxamer micelles solubilized the drugs at surprisingly high levels, on the order of more than 16 mg/mL for the three drug mixture. Compared to the solubility of a single hydrophobic drug in poloxamer micelles, combinations of the hydrophobic drugs show more than merely an additive effect, which is counterintuitive to general assumptions of hydrophobic drug solubility. Thus, it was unexpectedly found that the dual-agent micelles could be prepared such that the total drug loading was more than the maximum loading that was obtainable for single-agent micelles. This 'additive' effect with respect to drug loading does not result in substantial changes in the resulting diameter of the micelles until thrice the amount of drug as a three-drug formulation is used in the micelles (see Table 1 in Example 1 below).

Numerous conditions can be treated using the poloxamer micelle systems described herein. Combinations of active agents can be used in the individual micelles, or in collections of micelles each having a single type of drug in them. Simply mixed and co-encapsulated formulations allow for the administration of two different active agents with one administration, e.g., an IV infusion. Certain useful combinations and techniques are described in U.S. Pat. No. 7,221,562 (Rosen et al.). In other embodiments, single drug micelles (SDMs) can be administered sequentially to also provide the benefits of drug combination therapy using the biocompatible poloxamer micelles.

In some embodiments, the compositions are completely free of additives such as one or more of ethanol, dimethyl sulfoxide, or other organic solvents, phospholipids, castor oil, and castor oil derivatives. In other embodiments, the composition is substantially free of such components. As used herein, substantially free means that the composition contains less than about 2.5 wt. %, less than about 2 wt. %, less than about 1.5 wt. %, less than about 1 wt. %, less than about 0.5 wt. %, less than about 0.25 wt. %, or less than about 0.1 wt. %. In some embodiments, certain additives can increase the stability of the micelles. In one embodiment, a surfactant can be included in the micelle (e.g., in about 0.25 wt. % to about 2.5 wt. %). For example, a suitable surfactant can be a negatively charged phospholipid, such as polyethylene glycol conjugated distearoyl phosphatidyl-ethanolamine (PEG-DSPE).

The invention also provides a combination of three therapeutic agents, for example, gossypol (GSP), cyclopamine (CYP), and paclitaxel (PTX), in poloxamer or PEG-b-PCL micelles. Paclitaxel and cyclopamine could not be efficiently loaded in separate individual micelles (<1 mg/mL), but significant amount of both drugs could surprisingly be loaded (>6 mg/mL) in 3-in-1 micelles when incorporated with gossypol, potentially due to drug-specific inter-molecular interaction. The simultaneous solubilization of paclitaxel, cyclopamine, and gossypol for injection in an aqueous vehicle has not been available, thus the water soluble 3-in-1 poloxamer or PEG-b-PCL micelles containing gossypol, cyclopamine, and paclitaxel provide a new drug combination option for treating cancers, such as ovarian cancers.

The 3-in-1 micelles also showed gradual in vitro release kinetics of the three drugs over time. The cancer cell-killing efficacy of 3-in-1 micelles was evaluated in spheroid ES-2 ovarian cancer cells and the micelles were shown to penetrate and destroy ovarian cell spheroids, possibly by killing cancer stem cells. The therapeutic effect of the drug combination provides enhanced and/or synergistic inhibition and killing of cancer cells.

Accordingly, the invention provides a micelle composition comprising an aqueous solvent system and drug-encapsulating micelles, wherein the micelles comprise a plurality of polymers having an average molecular weight of about 1,000 to about 30,000, or about 1,500 to about 22,000, the polymers form one or more micelles, one or more micelles encapsulate a drug within their micelle structure, which drug is not covalently bound to the polymer, the drug is a gossypol compound, and the diameter of the micelles is about 15 nm to about 150 nm.

In one embodiment, the drug is R-(–)-gossypol.

In another embodiment, the drug is apogossypol.

In one embodiment, the polymer is a poloxamer, such as poloxamer 188.

In one embodiment, the polymer is a PEG-b-PCL polymer.

In one embodiment, the one or more micelles comprise a second drug, or a second and third drug, encapsulated within the micelles. In some embodiments, the second drug or third drug is a paclitaxel compound. In various embodiments, the second drug or third drug is a 17-AAG compound. In various embodiments, the second drug or third drug is a cyclopamine compound. In one specific embodiment, the micelles in the composition include the combination of gossypol, paclitaxel, and 17-AAG within individual micelles. In another specific embodiment, the micelles in the composition include the combination of gossypol, paclitaxel, and cyclopamine within individual micelles. In some embodiments, the gossypol, paclitaxel, and 17-AAG, or gossypol, paclitaxel, and cyclopamine, can be each individually incorporated into single-drug micelles, and the single-drug micelles can be combined into a single formulation for administration to a patient, or they can be administered to a patient separately and/or sequentially. The separate and/or sequential administration can also be carried out with any two-drug combination described herein.

In one embodiment, the concentration of the gossypol compound in the composition is about 1 mg/mL to about 6 mg/mL, about 1 mg/mL to about 5 mg/mL, about 2 mg/mL to about 6 mg/mL, about 3 mg/mL to about 6 mg/mL, or about 4 mg/mL to about 6 mg/mL.

In one embodiment, the concentration of the paclitaxel compound in the composition is about 1 mg/mL to about 7 mg/mL, about 1 mg/mL to about 6 mg/mL, about 2 mg/mL to about 7 mg/mL, about 3 mg/mL to about 7 mg/mL, or about 4 mg/mL to about 6 mg/mL.

In one embodiment, the concentration of the 17-AAG compound in the composition is about 1 mg/mL to about 7 mg/mL, about 1 mg/mL to about 6 mg/mL, about 2 mg/mL to about 7 mg/mL, about 3 mg/mL to about 7 mg/mL, or about 4 mg/mL to about 6 mg/mL.

In one embodiment, the concentration of the cyclopamine compound in the composition is about 1 mg/mL to about 7 mg/mL, about 1 mg/mL to about 6 mg/mL, about 2 mg/mL to about 7 mg/mL, about 3 mg/mL to about 7 mg/mL, or about 4 mg/mL to about 6 mg/mL.

In some embodiments, the concentration of each drug in the micelle composition is greater than about 3 mg/mL, about 4 mg/mL, or about 5 mg/mL. In various embodiments, each drug is present in its micelle at greater than about 5 wt. % of the mass of the polymer of the micelle. In some embodiments, the drug or combination of drugs is present in the micelles at about 5 wt. % to about 25 wt. % of the mass of the polymer of the micelles. In other embodiments, the drug or combination of drugs is present in the micelles at about 6 wt. % to about 20 wt. %, about 10 wt. % to about 20 wt. %, or about 12 wt. % to about 20 wt. % of the mass of the polymer of the micelles. The polydispersity index of the micelles can be less than about 0.3, for example, as determined by Dynamic Light Scattering (DLS) analysis.

The micelles can maintain an effective amount of encapsulated drugs within the micelles for significant periods of time at room temperature (~23° C.). In practice, the micelles can be prepared and administered within about eight hours of preparation. However, the micelles can also maintain more than about 60%, more than about 80%, or more than about 90%, of the micelle-encapsulated drugs within the micelles for more than 24 hours at room temperature. The micelle composition can also be free of ethanol, dimethyl sulfoxide, and castor oil or derivatives thereof.

The invention also provides a pharmaceutical composition that includes a micelle composition described herein, where the composition is formulated for intravenous or intraperitoneal administration. The aqueous carrier of such a composition can be, for example, saline or an aqueous carbohydrate solution.

In various embodiments, the micelles can encapsulate a synergistic two drug combination of a gossypol compound and a paclitaxel compound. In other embodiments, the micelles can encapsulate a synergistic two drug combination of a gossypol compound and a 17-AAG compound. In another embodiment, the micelles can encapsulate a synergistic three drug combination of a gossypol compound, a paclitaxel compound, and a 17-AAG compound. In other embodiments, the micelles can encapsulate a two drug combination of a gossypol compound and a cyclopamine compound. In another embodiment, the micelles can encapsulate a three drug combination of a gossypol compound, a paclitaxel compound, and a cyclopamine compound.

The gossypol compound can be, for example, (+/−)-gossypol; (−)-gossypol; (+)-gossypol; (+/−)-gossypolone; (−)-gossypolone; (+)-gossypolone; (+/−)-gossypol acetic acid; (−)-gossypol acetic acid; (+)-gossypol acetic acid; (+/−)-ethyl gossypol; (−)-ethyl gossypol; (+)-ethyl gossypol; (+/−)-hemigossypolone; (−)-hemigossypolone; (+)-hemigossypolone; (+/−)-apogossypol; (−)-apogossypol; (+)-apogossypol; (+/−)-apogossypol acetic acid; (−)-apogossypol acetic acid; (+)-apogossypol acetic acid; (+/−)-ethyl apogossypol; (−)-ethyl apogossypol; (+)-ethyl apogossypol; or a combination thereof.

In one specific embodiment, the invention provides a water soluble IV formulation comprising gossypol loaded poloxamer 188 micelles, wherein the formulation is free of organic solvents and surfactants.

In another embodiment, the invention provides a water soluble IV formulation comprising (i) gossypol and paclitaxel loaded poloxamer 188 micelles, (ii) gossypol and 17-AAG loaded poloxamer 188 micelles, or (iii) gossypol, paclitaxel, and 17-AAG loaded poloxamer 188 micelles, wherein the formulation exerts synergistic anticancer activity against lung cancer cells, for example, for the treatment of lung cancer. The formulations can be effective against other cancer tumors and cell types, as described below. Similar formulations can also include cyclopamine in place of 17-AAG, for example, for the inhibition, killing, or treatment of ovarian cancer cells or tumors. Additional formulations can be prepared using PEG-b-PCL in place of poloxamer 188.

Therapy Using Micelle Formulations.

The lack of suitable formulations has hindered the progression of therapeutic agents such as gossypol, paclitaxel, 17-AAG, and cyclopamine into clinical trials. Poloxamer micelle formulations of gossypol, paclitaxel, 17-AAG, and/or cyclopamine that do not require organic co-solvents or harsh surfactants have been developed. The formulations can solubilize significant amounts of each drug, on the order of 4-7 mg/mL, and the nanoscale dimensions further benefit tumor specificity of the drug through the EPR effect even in the absence of targeting ligands.

In some embodiments, the drug-loaded micelles can extravasate into tumor interstices, at which point the active agent-containing micelles release the drugs from the micelles due to the intracellular conditions. The active agent can then diffuse into tumor cells. Another aspect of the invention includes the micelles crossing leaky vasculature and endocytosing into tumor cells, and inhibiting the tumor cell growth, and/or killing cancer cells.

The invention thus provides methods for inhibiting the growth of cancer cells or killing cancer cells comprising contacting the cancer cells or a cancer tumor with an effective inhibitory or lethal amount of a composition or formulation as described herein. The contacting can be in vivo or in vitro.

The invention also provides a method of treating a hyperproliferative disease in a subject comprising administering to a subject in need of such treatment a therapeutically effective dose of a composition or formulation as described herein and optionally one or more additional active agents, the method used optionally in combination with radiation, heat, or both, wherein the hyperproliferative disease is thereby treated. The hyperproliferative disease (e.g., a cancer or a neoplastic disease) can be associated with overexpression of a Bcl-2 family member protein. The Bcl-2 family protein can be, for example, Bcl-2, Bcl-$X_L$, Mcl-1, A1/BFL-1, BOO-DIVA, Bcl-w, Bcl-6, Bcl-8, or Bcl-y.

The invention further provides a method of simultaneously administering two or three drugs to a patient that has, or has been diagnosed with, cancer that can be treated by administration of at least one of a gossypol compound, a paclitaxel compound, a 17-AAG compound, or a cyclopamine compound. The method can include administering an effective amount of a composition or formulation as described herein; wherein the cancer is thereby treated.

The invention additionally provides a method of sequentially administering two or three drugs to a patient that has, or has been diagnosed with, cancer that can be treated by administration of at least one of a gossypol compound, a paclitaxel compound, a 17-AAG compound, or a cyclopamine compound. The method can include administering an effective amount of a micelle composition as described herein; where the micelles individually encapsulate a gossypol compound;
followed by administering an effective amount of a second composition comprising a drug selected from a paclitaxel compound, a 17-AAG compound, a cyclopamine compound, or a combination thereof;
optionally followed by administering an effective amount of a third composition comprising a drug (i.e., that has not been previously administered in the method) selected from a paclitaxel compound, a 17-AAG compound, a cyclopamine compound, or a combination thereof; wherein the cancer is thereby treated. In such methods, the gossypol compound can be provided in a dose that sensitizes the subject to treatment by one or more of the therapeutic agents administered thereafter.

The cancer or the cancer cells can include, for example, brain tumor cells, breast cancer cells, colon cancer cells, head and neck cancer cells, lung cancer cells (SCLC or NSCLC), lymphoma cells, melanoma cells, neuroblastoma cells, ovarian cancer cells, pancreatic cancer cells, prostate cancer cells, or leukemia cells.

The cancer can be metastatic. In some embodiments, the cancer is a tumor and the treatment or amelioration results in regression of the tumor. The cancer can resistant to anticancer agents or radiation therapy. In some embodiments, the gossypol compound sensitizes the cancer to additional anticancer agents or radiation therapy.

In one embodiment, the gossypol compound and the additional anticancer agent or radiation are administered simultaneously. In another embodiment, the gossypol compound and the additional anticancer agent or radiation are administered sequentially.

In one embodiment, the gossypol compound is administered prior to another anticancer agent or radiation. In another embodiment, the gossypol compound is administered after another anticancer agent or radiation. In some embodiments, the gossypol compound and the additional anticancer agent or radiation are administered with different periodicities, different durations, different concentrations, and/or different administration routes.

In one embodiment, the gossypol compound is (−)-gossypol and the anticancer agent or radiation is selected from paclitaxel, docetaxel, 17-AAG, cyclopamine, cisplatin, radiation therapy, and combinations thereof. In some embodiments, the gossypol compound and the anticancer agent or radiation have a synergistic therapeutic effect.

Various diseases, disorders, and conditions can be treated by administering a pharmaceutical formulation of micelles described herein. Administration of these compositions can result in a reduction in the size and/or the number of cancerous growths in a patient, and/or a reduction in one or more corresponding associated symptoms. When administered in an effective amount, the compositions can produce a pathologically relevant response, such as inhibition of cancer cell proliferation, reduction in the size of a cancer or tumor, prevention of further metastasis, inhibition of tumor angiogenesis, and/or death of cancerous cells. The method of treating such diseases and conditions described herein includes administering a therapeutically effective amount of a composition of the invention to a patient. The method may be repeated as necessary, for example, daily, weekly, or monthly, or multiples thereof.

Conditions that can be treated include, but are not limited to, hyperproliferative diseases, including cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer; prostate cancer; pancreatic cancer; breast cancer sarcomas, such as fibrosarcoma, malignant fibrous histiocytoma, embryonal rhabdomyosarcoma, leiomyosarcoma, neurofibrosarcoma, osteosarcoma, synovial sarcoma, liposarcoma, and alveolar soft part sarcoma; neoplasms of the central nervous systems, particularly brain cancer; and/or lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, or T-cell anaplastic large cell lymphoma.

The micelle formulations carrying a gossypol compound, optionally in combination with a second or third active agent, can lower the threshold for cancer cells to undergo apoptosis in various tumor types. Such micelle formulations can provide single-agent cyto-reductive drug delivery systems for a variety of cancers, including chronic lymphocytic leukemia (CLL), non-Hodgkins lymphoma (NHL), and prostate cancer. In some embodiments, micelle formulations encapsulating a gossypol compound and a second active agent can be particularly effective for treating cancers such as hormone-refractory prostate cancer and non-small cell lung cancer (e.g., gossypol in combination with docetaxel), B-cell malignancies (e.g., gossypol in combination with rituximab), small cell lung cancer (e.g., gossypol in combination with topotecan), glioma (e.g., gossypol in combination with temozolomide, optionally in combination with radiotherapy) and esophageal cancer (e.g., gossypol in combination with docetaxel, 5-fluorouracil and radiotherapy).

The micelle formulation, for example, the formulation carrying a gossypol compound, cyclopamine, and paclitaxel, can be highly effective for treating cancers such as ovarian cancer. Ovarian cancer has a relatively high mortality rate (~55%). Despite good initial responses to chemotherapy, recurrence is common and usually fatal. Typically, the cancer disseminates into the peritoneal cavity as spheroids shed from the primary aggregate, which adhere to the peritoneum and then metastasize. These spheroids are usually resistant to chemotherapy. The combination of gossypol, cyclopamine, and paclitaxel has shown remarkable efficacy in destroying spheroids in an in vitro culture.

Non-cancer conditions that are characterized by cellular hyperproliferation can also be treated using the methods described herein. For example, the drugs can be administered according to the methods described herein to treat conditions that are characterized by cellular hyperproliferation. Illustrative examples of such non-cancer conditions, disorders, or diseases include, but are not limited to, atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and/or Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease, and type I diabetes. Other examples include vasculitis, e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis; gastrointestinal tract diseases, e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including idiopathic); eustachian tube diseases (e.g., strictures of all causes including idiopathic); as well as neurological diseases, fungal diseases, viral infections, and/or malaria.

The terms "treat", "treating", and "treatment" refer to any process, action, application, therapy, or the like, wherein a mammal, including a human being, is subject to medical aid with the object of improving the mammal's condition, directly or indirectly. Treatment can refer to the administration of an effective amount of a micelle composition as described herein. Treatment can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can in some cases extend to prophylaxis and include prevent, prevention, preventing, lowering, stopping or reversing the progression or severity of the condition or symptoms being treated. As such, the term "treatment" includes both medical, therapeutic, and/or prophylactic administration, in some embodiments.

The terms "effective amount" or "therapeutically effective amount" qualify the amount of a therapeutic agent necessary to relieve to some extent one or more of the symptoms of a condition, disease or disorder, including, but not limited to: 1) reducing the number of cancer cells; 2) reducing tumor size; 3) inhibiting (i.e., slowing to some extent, preferably stopping) cancer cell infiltration into peripheral organs; 3) inhibiting (i.e., slowing to some extent, preferably stopping) tumor metastasis; 4) inhibiting, to some extent, tumor growth; 5) relieving or reducing to some extent one or more of the symptoms associated with the disorder; and/or 6) relieving or reducing the side effects associated with the administration of active agents.

Thus, an effective amount refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a therapeutic agent or micelle composition described herein, e.g., that is effective to treat or prevent a disease or disorder, or to treat the symptoms of the disease or disorder, in a host. Thus, an effective amount generally means an amount that provides the desired effect.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition can be referred to as prevention or chemoprevention. The inhibition can be about 10%, about 25%, about 50%, about 75%, or about 90% inhibition, with respect to progression that would occur in the absence of treatment or contact.

For purposes of administration, for example, parenteral administration, sterile aqueous solutions of water-soluble salts (e.g., NaCl) can be employed. The aqueous solutions can be isotonic. Additional or alternative carriers may include sesame or peanut oil, as well as aqueous propylene glycol. Aqueous solutions may be suitably buffered, if necessary, and the liquid diluent can first be rendered isotonic with sufficient saline or glucose. These aqueous solutions are especially suitable for intravenous, intramuscular, subcutaneous, intraperitoneal, and intratumoral (IT) injection. Intratumoral injection can be especially helpful for certain types of therapy, such as the treatment of cancer, including prostate cancer. Appropriate sterile aqueous media can be purchased (e.g., Sigma-Aldrich Corporation, St. Louis, Mo.) or can be prepared by standard techniques well known to those skilled in the art.

When a pharmaceutical carrier, such as water or saline, dissolves the micelles such that the micelles can pass through a filter, the micelles are considered to be dissolved in a pharmaceutical "solution", thereby providing a formulation according to an embodiment of the invention. In one embodiment, the drug encapsulated micelles are formulated in a mixture that includes an aqueous carrier, such as saline, dextrose, and the like. For example, suitable carriers can be 0.9% NaCl solutions, or 5% aqueous saccharide solutions, such as a glucose solution. See also *Remington: The Science and Practice of Pharmacy*, D. B. Troy, Ed., Lippincott Williams & Wilkins (21$^{st}$ Ed., 2005) at pages 803-849.

The micelles can be formulated into a pharmaceutical solution and administered, for example, into the blood stream of a patient. The pharmaceutical solution can allow for delivery of a requisite amount of the drugs to the body within an acceptable time, for example, about 10 minutes, to about 3 hours, typically about 1 to about 2 hours, for example, about 90 minutes. The administration can be parenteral, for example, by infusion, injection, or by intravenous (IV) administration. Upon administration, the micelles can circulate intact, dissociate into individual polymer chains, release active agents (either by diffusion or micelle dissociation), distribute into tissue (e.g. tumors), and/or undergo renal clearance.

Using a pharmaceutical solution formulation of this invention, active agents such as gossypol, paclitaxel, and 17-AAG and/or other anticancer or cytotoxic agent may be administered in a dose ranging from about 4 mg/m$^2$ to about 4000 mg/m$^2$, depending on the frequency of administration. In one embodiment, a dosage regimen for the drug combinations can be about 400-500 mg/m$^2$ weekly, or about 450 mg/m$^2$ weekly. See Banerji et al., *Proc. Am. Soc. Clin. Oncol.*, 22, 199 (2003, abstract 797). Alternatively, a dose of about 300 mg/m$^2$ to about 325 mg/m$^2$, or about 308 mg/m$^2$ weekly can be administered to the patient. See Goetz et al., *Eur. J. Cancer*, 38

(Supp. 7), S54-S55 (2002). Another dosage regimen includes twice weekly injections, with doses ranging from about 200 mg/m$^2$ to about 360 mg/m$^2$ (for example, about 200 mg/m$^2$, about 220 mg/m$^2$, about 240 mg/m$^2$, about 250 mg/m$^2$, about 260 mg/m$^2$, about 280 mg/m$^2$, about 300 mg/m$^2$, about 325 mg/m$^2$, 340 mg/m$^2$, about 350 mg/m$^2$, or about 360 mg/m$^2$, depending on the severity of the condition and health of the patient). A dosage regimen that can be used for combination treatments with another drug, such as paclitaxel or docetaxel, can administer the two drugs every three weeks, with the dose of 17-AAG of about 500 mg/m$^2$ to about 700 mg/m$^2$, or up to about 650 mg/m$^2$ at each administration. Other concurrent dosing schedules that can be employed are described by Fung et al., *Clin. Cancer Res.* 2009; 15(17), 5389-5395. Other dosing schedules, conditions that can be treated by the compositions described herein, and the like are described by WO 2011/025838 (Tao et al.)

DEFINITIONS

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted, and one or more drugs, for example, one, two, or three different kinds of therapeutic agents.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges such moieties and substituents.

The term "contacting" refers to the act of touching, making contact, or of bringing to immediate or close proximity, including at the cellular or molecular level, for example, to bring about a physiological effect, a chemical reaction, or a physical change, e.g., in a solution, in a reaction mixture, in vitro, or in vivo.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation. Thus, provisos may apply to any of the disclosed categories or embodiments wherein any one or more disclosed embodiments or species may be excluded from certain categories, compositions, or embodiments.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Poloxamer Micelles Containing Gossypol and Gossypol Drug Combinations

Poloxamer micelles provide single or multiple drug delivery systems for difficult to solubilize drugs. Micelles composed of poloxamer 188 (Pluronic® F68) were used to prepare three-in-one nanocontainers for poorly water soluble drugs. In this example, gossypol, paclitaxel, and 17-AAG have been successfully solubilized in individual micelles to significant degrees of aqueous solubility. Single drug poloxamer micelles were also prepared.

Gossypol (GSP) is a Bcl-2 inhibitor. Paclitaxel is a well known chemotherapeutic, and 17-AAG is a potent Hsp90 inhibitor. However, each of these drugs is difficult to solubilize in water, which is necessary for effective delivery to patients. Using poloxamer micelles, these drugs have been solubilized together to provide a highly synergistic formulation for the treatment of cancers.

A key factor in the three-drug combination poloxamer micelles is the presence of gossypol. In the presence of gossypol, significant amounts of both paclitaxel and 17-AAG can also be solubilized in the micelle formulations. Surprisingly, the poloxamer micelles can also solubilize the diphenolic compound resveratrol, however the poloxamer micelles with only resveratrol and paclitaxel, or resveratrol and 17-AAG, were unstable, therefore the presence of gossypol appears to be important for maintaining the stability of these multiple drug micelles. Preparation of the gossypol-containing poloxamer micelles was carried out as follows.

Preparation of Drug-Loaded Poloxamer Micelles.

Figure 2:
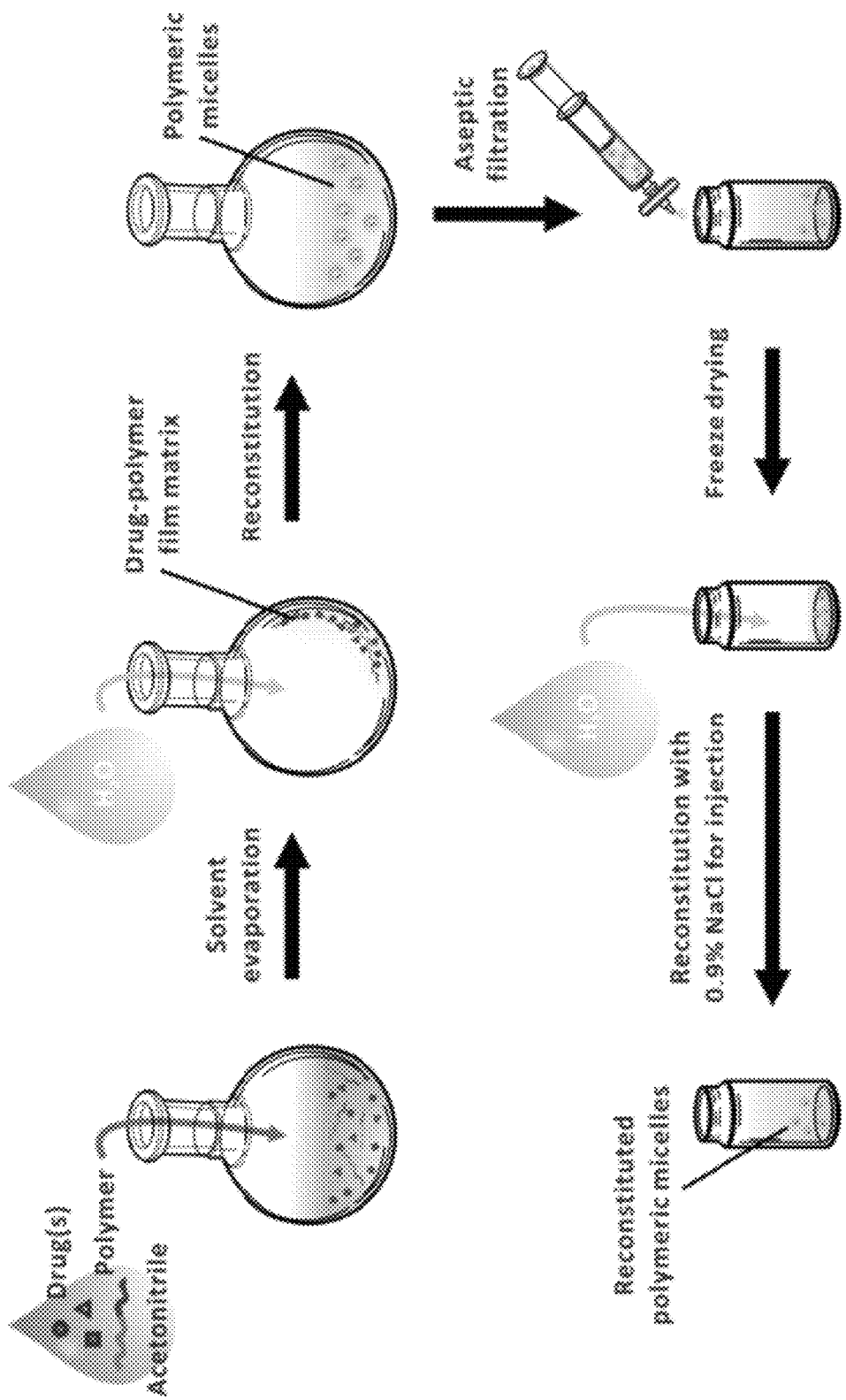
FIG. 2. A schematic representation of a method for preparing micelles and solubilizing hydrophobic drugs, according to one embodiment. In alternative embodiments, solvents other than acetonitrile can be employed. Additionally, other aqueous solvent systems can be used in the reconstitution step in place of 0.9% NaCl, such as pure water, glucose solutions, or buffered systems.

Poloxamer micelles containing gossypol and other drugs were prepared according to the solvent evaporation method and were reconstituted with deionized water, as schematically illustrated in FIG. 2. Briefly, for the singly-loaded poloxamer 188 micelles, 2.0 mg of each drug, i.e., paclitaxel, 17-AAG, and gossypol, and 21 mg of poloxamer 188 was dissolved using 1 mL acetone (or acetonitrile). The dissolved drug and polymer solution were transferred into 5 mL round bottom flask. The organic solvent was evaporated using rotary evaporator in a 60° C. water bath to provide a drug-polymer film. Deionized water (0.25 mL) was added to dissolve the drug-polymer film, inducing spontaneous micelle formation. Un-encapsulated drugs were removed by centrifugation at 13,000 rpm for 5 minutes and the micelles were then filtered using a 0.45 μm nylon filter. The filtered solution was analyzed by reverse-phase (RP) HPLC and Dynamic Light Scattering (DLS) for drug quantification and particle size determination, respectively (see Table 1).

For 2-in-1 poloxamer micelles, 2.0 mg of gossypol and paclitaxel or 2.0 mg of gossypol and 17-AAG were used for drug loading (for a total of 4 mg of drugs for loading). For 3-in-1 Pluronic micelles, 2.0 mg of each drug was used in the micelle formation procedure. Poloxamer 188 was unable to solubilize paclitaxel alone in stable micelles.

Quantification of Drug Concentration by RP-HPLC.

Figure 3:
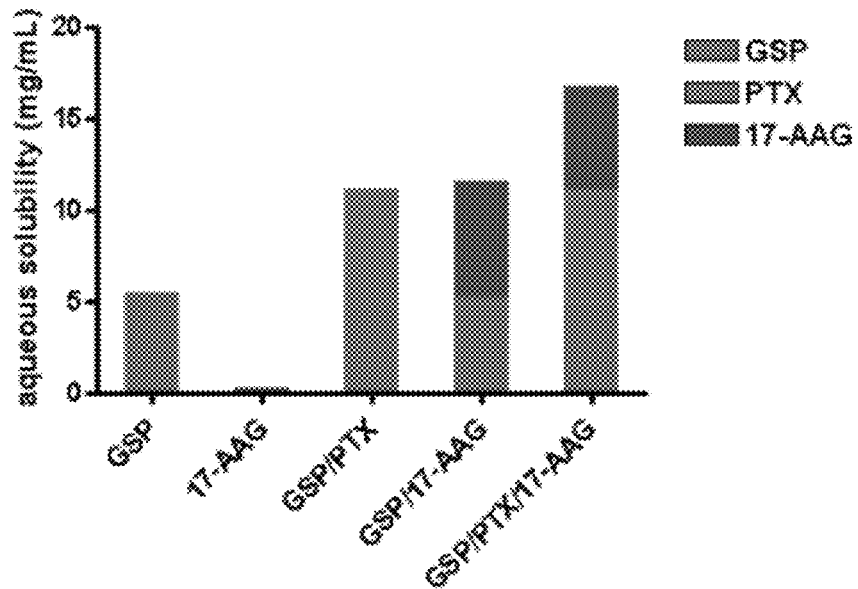
FIG. 3. A graph of the aqueous solubility (mg/mL) of anti-cancer drug loaded Poloxamer 188 micelles.

Drug concentration in the drug-loaded micelles was determined by RP-HPLC equipped with Shimadzu LC-20AT (HPLC pump), SIL-20AC (auto-sampler), CTO-20AC (column oven), and SPD-M20A (Photodiode array detector). A Zorbax RX-C8 column (4.6×250 mm, particle size 5 μm, Agilent) was used for the HPLC Analysis. The mobile phase was 25:75 mixture of deionized water (1% phosphoric acid) and acetonitrile by volume. The flow rate was 1.0 mL/min. Stop time for the analysis was set at 12.0 min. Gossypol, paclitaxel, and 17-AAG were monitored at 373, 227, 333 nm, respectively. Retention time of paclitaxel, 17-AAG, and gossypol was 4.0, 4.6, and 8.4 minutes. The concentration of paclitaxel, 17-AAG, and gossypol showed linearity at 12.5-200.0, 12.0-192.0, 12.0-192.0 μg/mL, respectively. The limit of detection of paclitaxel, 17-AAG, and gossypol was 0.5, 0.4, and 0.6 μg/mL, respectively. The resulting solubility of each drug was analyzed and the results are provided below in Table 1 (see also FIG. 3).

TABLE 1

Drug Solubilization Results for Poloxamer 188 Micelles.

| Anticancer agent | drug level in water (mg/mL) | % drug loading (wt. drug(s)/ wt. polymer) | Poloxamer 188 micelle diameter (nm ± SD) | PDI |
|---|---|---|---|---|
| Gossypol | 5.41 ± 0.14 | 6.44 ± 0.16 | 18.9 ± 0.5 | 0.215 ± 0.06 |
| Paclitaxel | — | — | — | — |
| 17-AAG | 0.21 | — | — | — |
| Gossypol | 4.65 ± 0.62 | 13.77 ± 1.12 | 55.6 ± 9.3 | 0.210 ± 0.03 |
| Paclitaxel | 6.53 ± 0.31 | | | |
| Gossypol | 5.18 ± 0.47 | 13.31 ± 1.08 | 21.6 ± 0.2 | 0.260 ± 0.07 |
| 17-AAG | 6.39 ± 0.50 | | | |
| Gossypol | 4.79 ± 0.28 | 19.91 ± 1.10 | 103.7 ± 7.2 | 0.113 ± 0.02 |
| Paclitaxel | 6.28 ± 0.18 | | | |
| 17-AAG | 5.86 ± 0.59 | | | |

For the quantification of drugs in the formulation, 10 μL of micelle solution was diluted with 990 μL of mobile phase and 10 μL of sample solution was injected into a RP-HPLC. The % drug loading, a measure of encapsulation efficiency, was calculated by following equation:

$$\% \text{ drug loading of each drug} = \frac{\text{drug concentration quantified by } RP\text{-}HPLC \text{ (as mg/mL)}}{\text{poloxamer concentration (as mg/mL)}} \times 100$$

Dynamic Light Scattering (DLS) Measurements.

The size of singly-loaded, 2-in-1, and 3-in-1 poloxamer micelles was determined by dynamic light scattering (ZETA-SIZER Nano-ZS, Malvern instrument). A He—Ne laser (4 mW, 633 nm) was used for the light source and scattered light was collected at 90 degree angles. Prior to the measurement, the micelle solution was diluted 20 times by adding deionized water. The measurement was performed at 25° C. in triplicate. Volume weighted size and polydispersity index (PDI) were reported for the characterization of particles as shown above in Table 1.

The micelle particle size increased when a second and/or third drug was added to the micelle formulation, however each of these formulations was quite stable. The increase in particle size was consistent when the micelles were prepared using other solvents.

Stability of the Micelle Solution.

The prepared poloxamer micelle solutions were stored at ambient temperature for 24 hours. The drugs remaining in the solution were quantified by RP-HPLC described above. The micelle solution was centrifuged at 13,000 rpm for 5 minutes and was then filtered with a 0.45 μm nylon filter to remove any drug aggregates in the micelle solution. The concentration of each drug was compared with that of each drug at initial preparation to estimate the stability of micelle solution. The data obtained are shown in Table 2 below.

TABLE 2

Drug loss from Pluronic F68 micelles after 24 hrs (reverse phase-HPLC).

| Anticancer agent | Initial drug level in water (mg/mL) | Drug level @ 24 hrs in water (mg/mL) | % w/w drug(s) @ 24 hr |
|---|---|---|---|
| Gossypol | 5.41 ± 0.14 | 5.70 ± 0.34 | 106.6 ± 7.5 |
| Paclitaxel | — | — | — |
| 17-AAG | 0.21 | — | — |
| Gossypol | 4.65 ± 0.62 | 3.84 ± 1.14 | 82.4 ± 19.4 |
| Paclitaxel * | 6.53 ± 0.31 | 4.11 ± 2.26 | 63.4 ± 35.4 |
| Gossypol | 5.18 ± 0.47 | 5.11 ± 0.51 | 98.8 ± 4.7 |
| 17-AAG | 6.39 ± 0.50 | 6.34 ± 0.60 | 99.1 ± 1.7 |
| Gossypol | 4.79 ± 0.28 | 4.86 ± 0.05 | 101.6 ± 5.0 |
| Paclitaxel | 6.28 ± 0.18 | 6.36 ± 0.18 | 101.3 ± 1.1 |
| 17-AAG | 5.86 ± 0.59 | 5.77 ± 0.53 | 102.3 ± 1.4 |

* Stable for >10 hours at room temperature (by visual appearance).

In vitro Cytotoxicity.

Cytotoxicity was determined using a resazurin cell viability assay. A549 cells were cultured in RPMI1640, supplemented with 10% FBS, 100 IU/mL penicillin, 100 μg/mL streptomycin, and 2 mM of L-glutamine. The cells were incubated at 37° C., 5% $CO_2$ atmosphere. Exponentially grown cells were detached from the T-flask by adding a Trypsin-EDTA solution. The number of cells were counted using a microscope and an appropriate number of cells (3000-5000) cells were plated into 96 well-plates and incubated 37° C. for 24 hours.

Each drug was dissolved at 10 mM as a stock solution using dimethyl sulfoxide (DMSO). For the two drug combinations, the molar ratio of gossypol and paclitaxel or gossypol paclitaxel was fixed at 1:1. For the three drug combination, the molar ratio of gossypol, paclitaxel, and 17-AAG was fixed at 5:5:1. The stock solution was diluted with cell culture media and the final concentration of DMSO was less than 0.1%. The cells were exposed at 0.1, 1, 10, 100, 1000, 10000 nM of single drug and drug combinations for 72 hours. The fraction of viable cells were determined using a Cell titer Blue® dye assay (Promega, USA) by monitoring using fluorescence at 590 nm (emission). The inhibitory drug concentration ($IC_{50}$) was determined by the median-effect equation using compusyn software (Combosyn Inc., US). The determination of $IC_{50}$ was performed in three independent experiments. The resulting data is shown in Table 3.

TABLE 3

Cytotoxicity of Gossypol and Combinations Against A549 NSCLC Cells.

| Active Agent | $IC_{50}$ | Molar ratio |
|---|---|---|
| Gossypol | 6.5 ± 3.4 μM | — |
| Paclitaxel | 616 ± 418 nM | — |
| 17-AAG | 221 ± 77 nM | — |
| Gossypol Paclitaxel | 92 ± 26 nM | 1:1 |
| Gossypol 17-AAG | 149 ± 79 nM | 1:1 |
| Gossypol Paclitaxel 17-AAG | 49 ± 19 nM | 5:5:1 |

(n = 3, mean ± SD)

Combination Index (CI) Analysis.

Figure 4:
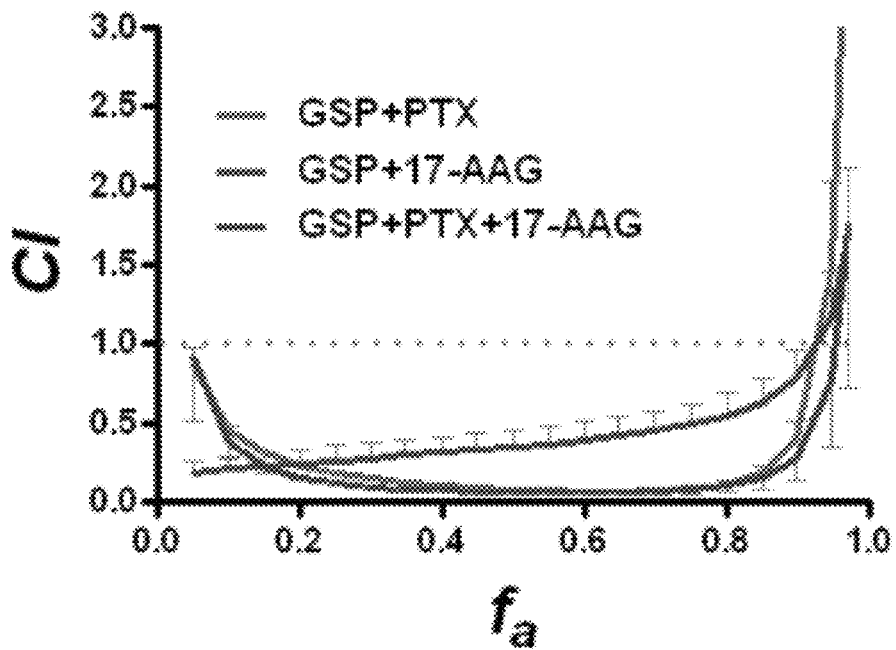
FIG. 4. fa-CI plot for the in vitro cytotoxicity of drug combinations vs. the A549 NSCLC cell line ($f_a$ is the fraction of affected cells; CI is the Combination Index); GSP=gossypol; PTX=paclitaxel (n=3, mean±SEM).

In free drug experiments, a significant amount of synergy was found for the two drug combinations of gossypol+paclitaxel, and gossypol+17-AAG, and for the three drug combination of gossypol+paclitaxel+17-AAG, as illustrated in FIG. 4.

The half maximal inhibitory drug concentration ($IC_{50}$) was determined by the median-effect equation:

$$f_a = \frac{1}{\left[1 + \left(\frac{IC_{50}}{D}\right)^m\right]}$$

using CompuSyn software (Version 1.0, ComboSyn Inc., US). In the median-effect equation, $f_a$ is the fraction of affected cells; D is drug concentration; and m is the Hill slope or kinetic order. $IC_{50}$ values for gossypol (GSP), paclitaxel (PTX), 17-AAG, and combinations were determined from three independent growth inhibition curves and the results are represented as a mean±standard deviation.

CI analysis based on Chou-Talalay method (see Chou, Cancer Res. 2010, 70(2), 440-446) was performed using the CompuSyn software for the GSP, PTX, and 17-AAG combinations, determining synergistic, additive, or antagonistic cytotoxic effects against A549 non-small lung cancer cells. Briefly, $f_a$ was determined as a function of D by the median-effect equation, varying doses from 5% of affected cells ($IC_5$) to 97% of affected cells ($IC_{97}$).

CI values at each $f_a$ for two-drug combinations were calculated using the following equation:

$$CI = \frac{(D)_1}{(D_x)_1} + \frac{(D)_2}{(D_x)_2}$$

where $(D_x)_1$ and $(D_x)_2$ represent the $IC_x$ value of drug 1 alone and drug 2 alone, respectively. $(D)_1$ and $(D)_2$ represent the concentration of drug 1 and drug 2 at the $IC_x$ value (x % growth inhibition). For the three drug combination, the following equation was used by simply adding a third term:

$$CI = \frac{(D)_1}{(D_x)_1} + \frac{(D)_2}{(D_x)_2} + \frac{(D)_3}{(D_x)_3}$$

Values of CI>1 represent antagonism, values of CI=1 represent additive, and values of CI<1 represent synergism. At constant drug combination ratios, $f_a$ versus CI plots for two- and three-drug combinations were obtained with GraphPad prism software (Version 5.0, www.graphpad.com, US). The fa-CI plot was prepared for the two- and three-drug combinations and synergistic effects were observed, as illustrated in FIG. 4 and the corresponding data shown in Table 4.

TABLE 4

Combination Index (CI) of Specific Drug Combinations vs. A549 NSCLC Cells.

| | CI | Molar ratio |
|---|---|---|
| Gossypol + Paclitaxel | 0.08 ± 0.02 | 1:1 |
| Gossypol + 17-AAG | 0.35 ± 0.18 | 1:1 |
| Gossypol + Paclitaxel + 17-AAG | 0.06 ± 0.02 | 5:5:1 |

The data shown in Table 4 confirms that each of the drug combinations has significant synergistic anti-tumor efficacy at 50% of cell growth inhibition in A549 cells. The data shown in FIG. 4 confirms that the synergistic effects are not restricted to a range near 50% of cell growth inhibition (Fa=0.5). The CI values at different fractions of affected cells (fa=0.05 to 0.97) were plotted to obtain the fa-CI plot of FIG. 4, which indicates a wide range of synergistic activity of the drug combinations across the various fractions of affected cells.

Example 2

Compositions for Treating Ovarian Cancer

Another embodiment of the invention provides concurrent combination therapy using polymeric micelles carrying three potent therapeutic agents: gossypol, cyclopamine, and paclitaxel. This combination can maximize efficacy and reduce drug resistance by solubilizing the highly hydrophobic drugs in an aqueous solution, minimizing IV injection volume and achieving a highly synergistic cancer cell-killing efficiency. Poly(ethylene glycol)-block-poly(ε-caprolactone) (PEG-b-PCL) assembles into nanoparticles (micelles) that take up a chemotherapeutic agent (paclitaxel), a Hedgehog pathway inhibitor (cyclopamine), and a Bcl-2 inhibitor (gossypol) (FIG. 5). The combination of paclitaxel, cyclopamine, and gossypol can also be solubilized by poloxamer 188 polymers to form drug combination micelles.

A variety of PEG-b-PCL polymers can be used to prepare the micelle described herein, such as those illustrated in FIG. 5. One suitable and effective polymer is a $PEG_{5k}$-b-$PCL_{10k}$ polymer, which was used in the experiments of this example. PEG-b-PCL and poloxamer polymers can also be used to prepare the micelles, for example, as described below.

A. Three-in-One PEG-b-PCL Micelles Prepared by a Nanoprecipitation Method.

PEG-b-PCL ($M_n$ of PEG=5,000 g/mol; $M_n$ of PCL=10,000 g/mol; $M_w/M_n$=1.3), PTX, CYP, and GSP were dissolved in 1 mL of acetone, followed by a rapid addition of 1 mL of 0.9% saline with vigorous mixing. Acetone was evaporated from the aqueous micelle solution under reduced pressure using a rotatory evaporator at 60° C. The aqueous micelle solution was centrifuged for 5 min at 10,000 g to remove insoluble drugs and passed through a 0.45 μm nylon syringe filter.

B. Three-in-One Poloxamer 188 Prepared by a Solvent Evaporation Method.

Poloxamer 188 Pastile, PTX, CYP, and GSP were dissolved in 1 mL of acetone. Acetone was evaporated from the aqueous micelle solution under reduced pressure using a rotatory evaporator at 60° C. The thin film of "polymer plus drug mixture" was reconstituted with 1 mL of 0.9% saline at 60° C. The aqueous micelle solution was centrifuged for 5 min at 10,000 g to remove insoluble drugs and passed through 0.45 a μm nylon syringe filter.

Figure 6:
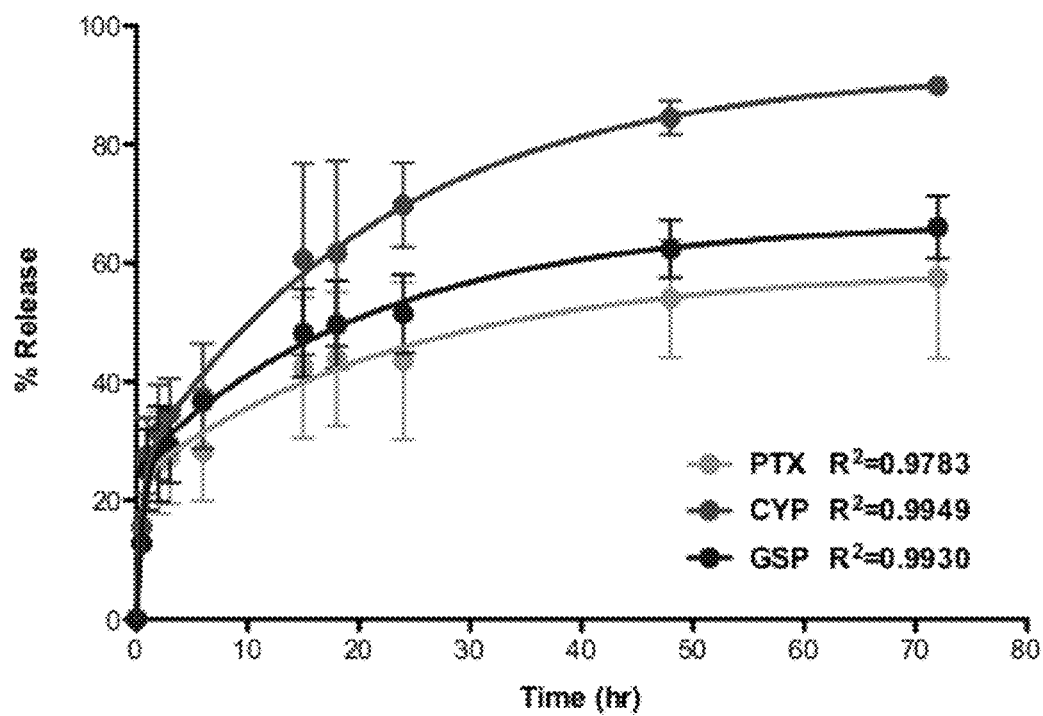
FIG. 6. In vitro release kinetics of three drugs from 3-in-1 PEG-b-PCL micelles.

Paclitaxel and cyclopamine could not be efficiently loaded in separate individual micelles (<1 mg/mL), but significant amount of both drugs could be loaded (>6 mg/mL) in 3-in-1 micelles when incorporated with gossypol, (Tables 2-1 and 2-2). These three-in-one micelles also showed gradual in vitro release kinetics of the three drugs over time (FIG. 6).

The content of PTX, CYP, and GSP in PEG-b-PCL micelles described in Tables 2-1 and 2-2 was quantified by reverse-phase HPLC (RP-HPLC) analysis, using $C_8$ rapid resolution cartridge (4.6 mm×75 mm, 3.5 mm). Samples for RP-HPLC were prepared by adding acetonitrile (ACN) into each micelle to break it apart and quantify drugs dissolved in ACN. The separation of PTX, CYP, and GSP was performed in isocratic mode with mobile phase consisting of acetonitrile (55% including 0.1% TFA) and double-distilled $H_2O$ (45% including 0.1% TFA). PTX (227 nm), CYP (204 nm), and GSP (373 nm) eluted at 2.7 min, 1.9 min, and 10.6 min, respectively.

TABLE 2-1

Drug Loading of $PEG_{5k}$-b-$PCL_{10k}$ micelles.

| Polymer (mg/ml) | PTX (mg/ml) | CYP (mg/ml) | GSP (mg/ml) | Encapsulation efficiency (%) | Loading efficiency (%) |
|---|---|---|---|---|---|
| 10 | 0.4 ± 0.2 | — | — | 40 ± 20 | 4 ± 2 |
| 10 | — | 0.05 ± 0.03 | — | 5 ± 3 | 1 ± 3 |
| 10 | — | — | 1.78 ± 0.08 | 89 ± 4 | 18 ± 1 |
| 10 | 0.55 ± 0.17 | — | 0.57 ± 0.09 | 56 ± 13 | 11 ± 3 |
| 10 | 0.81 ± 0.09 | 0.14 ± 0.06 | — | 40 ± 6 | 10 ± 2 |
| 10 | — | 1.50 ± 0.50 | 1.17 ± 0.52 | 99 ± 34 | 27 ± 10 |
| 10 | 0.86 ± 0.12 | 1.03 ± 0.02 | 0.94 ± 0.07 | 94 ± 7 | 28 ± 2 |
| 20 | 1.48 ± 0.2 | 1.25 ± 0.11 | 1.12 ± 0.15 | 86 ± 10 | 19 ± 2 |
| 100 | 4.29 ± 0.31 | 4.47 ± 0.38 | 4.13 ± 0.50 | 86 ± 8 | 13 ± 1.19 |
| 200 | 3.82 ± 0.55 | — | — | 63 ± 9 | 2 ± 0.3 |
| 200 | — | 1.22 ± 0.10 | — | 20 ± 2 | 1 ± 0.1 |
| 200 | — | — | 2.32 ± 0.49 | 39 ± 8 | 1 ± 0.2 |
| 200 | 3.57 ± 0.44 | — | 2.70 ± 0.49 | 52 ± 8 | 3 ± 0.5 |
| 200 | 2.79 ± 0.19 | 0.89 ± 0.03 | — | 31 ± 2 | 2 ± 0.1 |
| 200 | — | 3.23 ± 0.99 | 3.17 ± 0.21 | 53 ± 10 | 3 ± 1 |
| 200 | 6.30 ± 0.53 | 6.20 ± 0.49 | 6.24 ± 0.54 | 84 ± 7 | 9 ± 1 |

Encapsulation efficiency (% w/w) = (Drug loaded/Drug added) × 100.
Loading efficiency (% w/w) = (Drug loaded/Polymer added) × 100.

In Table 2-1, the encapsulation efficiency shows that the two- and three-drug combinations that include gossypol can be prepared on practical levels for administering to patients needing such treatment. The three-drug combination of PTX/CYP/GSP is solubilized at the PEG-b-PCL polymers at significantly high levels, more than 6 mg/mL for each of the three drugs. Without the presence of gossypol, even at 200 mg/mL of polymer, the highest solubility level of PTX is only 3.8 mg/mL and the highest solubility level of CYP is about 1.2 mg/mL, far lower than the 6.3 and 6.2 mg/mL, respectively, in the presence of gossypol.

TABLE 2-2

Drug Loading of poloxamer 188 micelles.

| Polymer (mg/ml) | PTX (mg/ml) | CYP (mg/ml) | GSP (mg/ml) | Encapsulation efficiency (%) | Loading efficiency (%) |
|---|---|---|---|---|---|
| 10 | 0.014 ± 0.002 | — | — | 1 ± 0.2 | 0.1 ± 0.02 |
| 10 | — | 0.012 ± 0.002 | — | 1 ± 0.2 | 0.1 ± 0.02 |
| 10 | — | — | 1.58 ± 0.23 | 79 ± 11 | 16 ± 2 |
| 10 | 0.87 ± 0.09 | — | 0.74 ± 0.37 | 81 ± 9 | 16 ± 2 |
| 10 | 0.01 ± 0.001 | 0.03 ± 0.001 | — | 2 ± 0.1 | 0.4 ± 0.03 |
| 10 | — | 0.16 ± 0.04 | 0.07 ± 0.03 | 12 ± 1 | 2 ± 0.1 |
| 10 | 0.38 ± 0.12 | 0.21 ± 0.07 | 0.15 ± 0.02 | 25 ± 6 | 7 ± 1 |
| 20 | 0.63 ± 0.14 | 0.27 ± 0.07 | 0.41 ± 0.003 | 22 ± 5 | 7 ± 1 |
| 100 | 4.11 ± 0.58 | 3.55 ± 0.18 | 3.44 ± 0.25 | 74 ± 9 | 11 ± 2 |
| 200 | 0.02 ± 0.01 | — | — | 0.3 ± 0.2 | 0.01 ± 0.005 |
| 200 | — | 0.07 ± 0.02 | — | 1 ± 0.3 | 0.04 ± 0.01 |
| 200 | — | — | 4.47 ± 0.27 | 75 ± 5 | 2 ± 0.1 |
| 200 | 3.49 ± 0.39 | — | 3.26 ± 0.22 | 56 ± 10 | 3 ± 0.3 |
| 200 | 0.01 ± 0.01 | 0.08 ± 0.02 | — | 0.8 ± 0.3 | 0.05 ± 0.02 |
| 200 | — | 3.5 ± 0.3 | 3.1 ± 0.34 | 55 ± 5 | 3 ± 0.3 |
| 200 | 6.41 ± 0.63 | 5.09 ± 0.29 | 5.73 ± 0.42 | 82 ± 7 | 9 ± 1 |

Encapsulation efficiency (% w/w) = (Drug loaded/Drug added) × 100.
Loading efficiency (% w/w) = (Drug loaded/Polymer added) × 100.

The results shown in Table 2-2 show an even more drastic contrast between micelles that include gossypol and those that do not. Without the presence of gossypol, even at 200 mg/mL of polymer, the highest solubility level of PTX is only about 0.02 mg/mL and the highest solubility level of CYP is about 0.07 mg/mL, far lower than the 6.4 and 5.1 mg/mL, respectively, in the presence of gossypol.

As shown below in Table 2-3, 1-in-1, 2-in-1, and 3-in-1 $PEG_{5k}$-b-$PCL_{10k}$ micelles using 200 mg of polymers were prepared (see Table 2-1) and the aqueous micelle solution was centrifuged for 5 min at 10,000 g over time (day 0-1) to quantify remaining drugs in stable aqueous micelle solution. Supernatant was collected and drug contents were analyzed by RP-HPLC analysis.

TABLE 2-3

PEG-b-PCL Micelle Stability Tests (Drug Quantification).

| | | % Remaining | |
|---|---|---|---|
| Micelles | Drugs | Day 0 | Day 1 |
| 1-in-1 | PTX | 100 ± 9.3 | 34.3 ± 3.1 |
| | CYP | 100 ± 10.6 | 96.3 ± 5.0 |
| | GSP | 100 ± 4.7 | 89.4 ± 3.3 |
| 2-in-1 | PTX | 100 ± 12.6 | 27.0 ± 2.9 |
| | CYP | 100 ± 11.3 | 97.4 ± 5.7 |
| | PTX | 100 ± 9.4 | 66.8 ± 4.1 |
| | GSP | 100 ± 4.4 | 97.0 ± 2.5 |
| | CYP | 100 ± 8.2 | 91.0 ± 5.3 |
| | GSP | 100 ± 4.9 | 89.8 ± 3.7 |
| 3-in-1 | PTX | 100 ± 4.7 | 99.3 ± 2.2 |
| | CYP | 100 ± 6.1 | 36.8 ± 1.5 |
| | GSP | 100 ± 3.8 | 82.3 ± 2.6 |

As shown below in Table 2-4, 1-in-1, 2-in-1, and 3-in-1 $PEG_{5k}$-b-$PCL_{10k}$ micelles using 200 mg of polymers and 10× decreased drug loading (vs. Table 2-3) were prepared and the aqueous micelle solution was centrifuged for 5 min at 10,000 g over time (day 0-1) to quantify remaining drugs in stable micelle solution. Supernatant was collected and drug contents were analyzed by RP-HPLC analysis. The reduction in drug concentration provided an increase of micelle stability over a 24 hour period of time.

TABLE 2-4

PEG-b-PCL Micelle Stability Tests (Drug Quantification) (10× decreased drug loading).

| | | % Remaining | |
|---|---|---|---|
| Micelles | Drugs | Day 0 | Day 1 |
| 1-in-1 | PTX | 100 ± 8.3 | 89.7 ± 5.2 |
| | CYP | 100 ± 7.9 | 96.0 ± 4.4 |
| | GSP | 100 ± 5.6 | 98.3 ± 3.6 |
| 2-in-1 | PTX | 100 ± 6.2 | 90.7 ± 5.1 |
| | CYP | 100 ± 5.5 | 94.3 ± 5.3 |
| | PTX | 100 ± 6.3 | 93.2 ± 4.9 |
| | GSP | 100 ± 7.1 | 89.5 ± 3.8 |
| | CYP | 100 ± 5.9 | 96.5 ± 4.4 |
| | GSP | 100 ± 4.1 | 95.4 ± 3.6 |
| 3-in-1 | PTX | 100 ± 3.6 | 87.9 ± 2.7 |
| | CYP | 100 ± 4.2 | 87.7 ± 2.6 |
| | GSP | 100 ± 3.8 | 81.0 ± 3.0 |

As shown below in Table 2-5, CYP/GSP(2-in-1)- and PTX/CYP/GSP(3-in-1)-incorporated poloxamer 188 micelles using 200 mg of polymers were prepared (see Table 2-2) and the aqueous micelle solution was centrifuged for 5 min at 10,000 g over time (day 0-1) to quantify remaining drugs in stable micelle solution. Supernatant was collected and drug contents were analyzed by RP-HPLC analysis. The particle size (by DLS) was measured and no significant changes were observed over time. However, the color of the solution (bright yellow due to GSP) darkened over time for both the CYP/GSP-incorporated micelle solution and PTX/CYP/GSP-incorporated micelle solution. This change could be a result of oxidation of GSP due to the presence of water in the more hydrophilic poloxamer polymers (relative to PEG-b-PCL). However, the poloxamer polymer micelles showed excellent stability over a 24 hour period of time as determined by the RP-HPLC and DLS analyses.

TABLE 2-5

Poloxamer 188 Micelle Stability Tests
(Quantification & Particle Size).

| Micelles | Drugs | Day 0 % Remaining | Day 0 Z-Average (nm) (PDI) | Day 1 % Remaining | Day 1 Z-Average (nm) (PDI) |
|---|---|---|---|---|---|
| CYP/ | CYP | 100 ± 7.4 | 36.1 ± 0.02 | 106.9 ± 3.4 | 37.0 ± 0.01 |
| GSP | GSP | 100 ± 9.2 | (0.14 ± 0.10) | 97.9 ± 1.7 | (0.11 ± 0.01) |
| PTX/ | PTX | 100 ± 5.8 | 72.3 ± 0.1 | 103.2 ± 2.3 | 76.5 ± 0.01 |
| CYP/ | CYP | 100 ± 4.9 | (0.08 ± 0.01) | 101.2 ± 2.3 | (0.08 ± 0.01) |
| GSP | GSP | 100 ± 5.1 | | 101.5 ± 3.5 | |

Drug release kinetics of 3-in-1 $PEG_{5k}$-b-$PCL_{10k}$ micelles was profiled by a dialysis method. An aqueous micelle solution was loaded into dialysis cassettes (20,000 MWCO, n=4) and the cassettes were placed in 2 L of 0.9% saline at 37° C. with stirring. Samples were withdrawn from the cassettes at various time points and the cassettes were replenished with fresh saline. Withdrawn samples were analyzed for the amounts of drugs in $PEG_{5k}$-b-$PCL_{10k}$ micelles by RP-HPLC. The results are illustrated in FIG. 6.

In Vitro Cytotoxicity.

Figure 7:
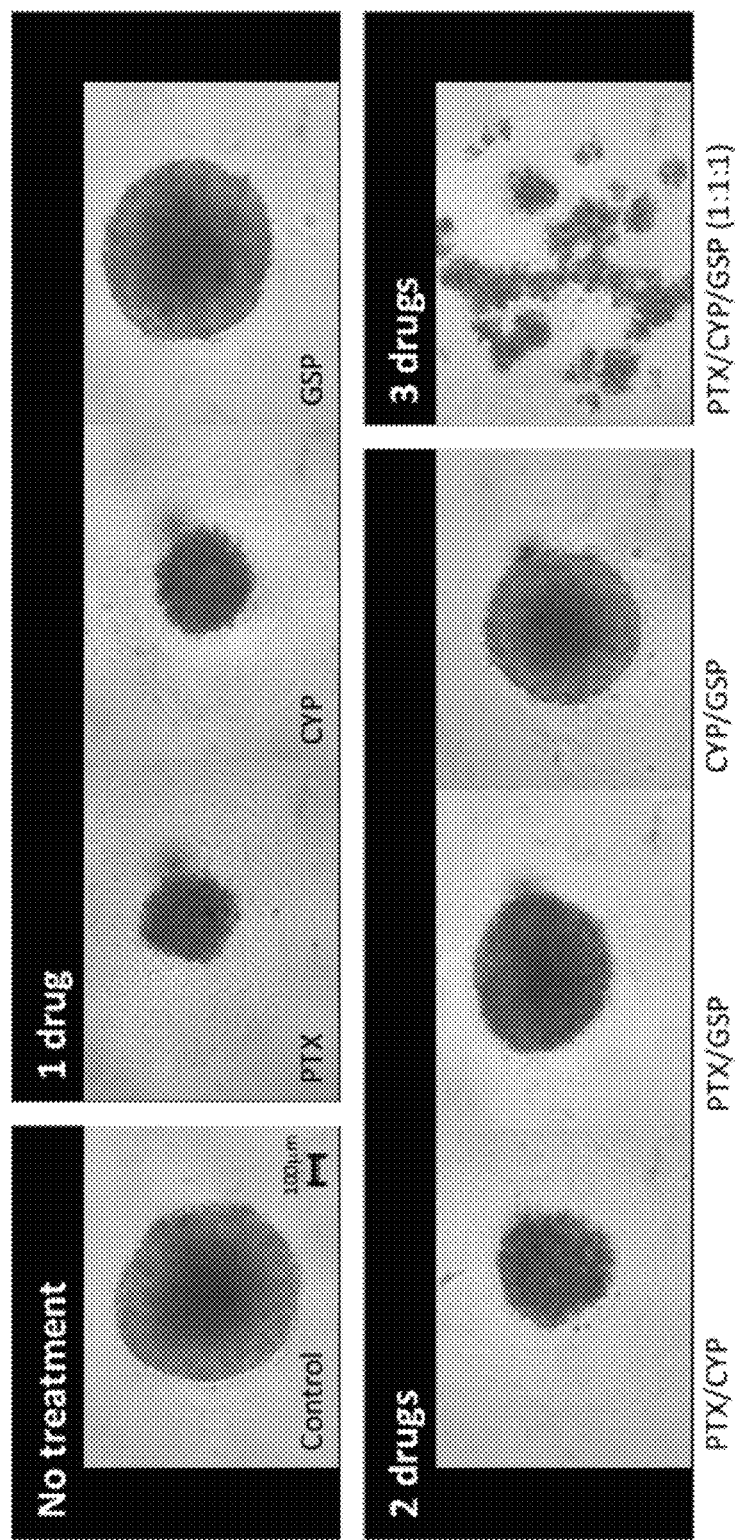
FIG. 7. ES-2 cells seeded on agarose-coated well plates for 96 hours before micelle treatment. Images obtained 72 hours post treatment. Representative images collected by inverted light microscope are shown for five independent samples per group.

The effects of single agents and 2- and 3-drug combinations in PEG-b-PCL micelles ([Total drug]=1 mM) on ES-2 ovarian multicellular spheroids are shown in FIG. 7. When treating the cells, a total of 1 µM drugs was used in each experiment, where single drug treatments used 1 µM of PTX, 1 µM of CYP, or 1 µM of GSP. The 2-drug combinations used 0.5 µM of PTX+0.5 µM of CYP; 0.5 µM of PTX+0.5 µM of GSP; and 0.5 µM of CYP+0.5 µM of CYP. The 3-drug combination used 0.33, 0.33, and 0.33 µM of PTX, CYP, and GSP, respectively (FIG. 7).

Luc-ES-2 cells (1,000 cells/well) were plated on agarose-coated 96 well plates and incubated for 96 hours before micelle treatment. 1-in-1, 2-in-1, and 3-in-1 $PEG_{5k}$-b-$PCL_{10k}$ micelles, representing total drug concentration of 1000, 100, 10, 1, 0.1 nM, were treated on luc-ES-2 spheroids. Surviving cells after treatment were quantified by scanning bioluminescence of luc-ES-2 cells (IVIS optical imaging system).

The images of FIG. 7 were collected using an inverted light microscope on spheroids treated with $PEG_{5k}$-b-$PCL_{10k}$ micelles representing 1000 nM of total drug concentration. In advance, to obtain luciferase-expressing ES-2 cells, ES-2 cells were transfected with pGL4 with neomycin resistance using Lipofectamine 2,000. Selection of luc-ES-2 was done using G418 (700 µg/mL) for a month and a linear relationship between the number of cells and corresponding bioluminescence was achieved.

The cancer cell-killing efficacy of 3-in-1 micelles was evaluated in spheroid ES-2 ovarian cancer cells (FIG. 7), and it was observed that 3-in-1 micelles could penetrate cell spheroids and unusually destroyed ovarian cell spheroids, potentially by killing cancer stem cells. While gossypol alone micelles had little effect on the ovarian spheroids, in combination with PTX and CYP, the micelles were able to break apart the spheroid, kill cancer cells, and significantly reduce the overall size of the tumor components. Thus, the water soluble 3-in-1 PEG-b-PCL or poloxamer 188 micelles containing paclitaxel, cyclopamine, and gossypol are a highly effective formulation for killing cancer cells and treating ovarian cancers.

As shown in FIG. 7, the spheroids broke apart and shrank in the 3-drug combination group. The bioluminescence of surviving cells was scanned to show the image of the 3-drug combination. A disadvantage of analysis using bioluminescence is that when a multilayer system is destroyed into several monolayer systems, the bioluminescence can appear relatively stronger because of the resulting presence of multiple monolayers. A bioluminescence scanner can read more bioluminescence signals in monolayers than in a multilayer as a result of the 2D-monolayered cells being detected more easily relative to signals in 3D structured cells.

Relatively evenly-distributed monolayered cells that were destroyed by drugs can be more exposed to the camera system and can provide higher values relative to signals for spheroids (while not reflecting total cell killing). The effect of the 3-in-1 micelles is therefore greater than is shown by the bioluminescence analysis, thus the 3-drug combination showed remarkable activity by destroying and dispersing the typically drug-resistant ovarian multicellular spheroid tumors.

Furthermore, it is well known that GSP itself does not have significant anticancer efficacy, and CYP itself is not toxic compared to PTX. However, in the 3-drug combination, even though only 0.33 µM of PTX was used (the most toxic component at one-third the concentration of the single drug PTX treatment), high anticancer efficacy in monolayer cells was still achieved. Combination index analysis (e.g., from Cellti-ter blue data) can further show the enhanced activity of the 3-in-1 combination micelles.

Cell Cytotoxicity ($IC_{50}$) of PTX/CYP/GSP in ES-2 Cells.

Table 2-6 below shows the effects of single agents and 2- and 3-drug combinations of $PEG_{5k}$-b-$PCL_{10k}$ micelles. Bioluminescence of surviving cells was quantified and $IC_{50}$ value was calculated by using Compusyn. Both the Celltiter blue assay and the bioluminescence assay provided similar values.

TABLE 2-6

$IC_{50}$ values (nM) of ES-2 ovarian multicellular spheroids and monolayer cells.

| Cells | PTX | CYP | GSP | PTX/CYP | CYP/GSP | GSP/PTX | PTX/CYP/GSP |
|---|---|---|---|---|---|---|---|
| Monolayer (BLI) | 12.0 | 239.7 | >100,000 | 26.7 | 18,791 | 40.4 | 51.4 |
| Monolayer (Celltiter Blue) | 13.0 | 244.6 | >100,000 | 29.8 | 32,625 | 62.2 | 57.9 |
| Spheroids (BLI) | 8.7 | 64.8 | 4,823 | 62 | 2,550 | 108.4 | 101.2 |

Bioluminescence (BLU)—In Vivo Anticancer Efficacy.

Figure 8:
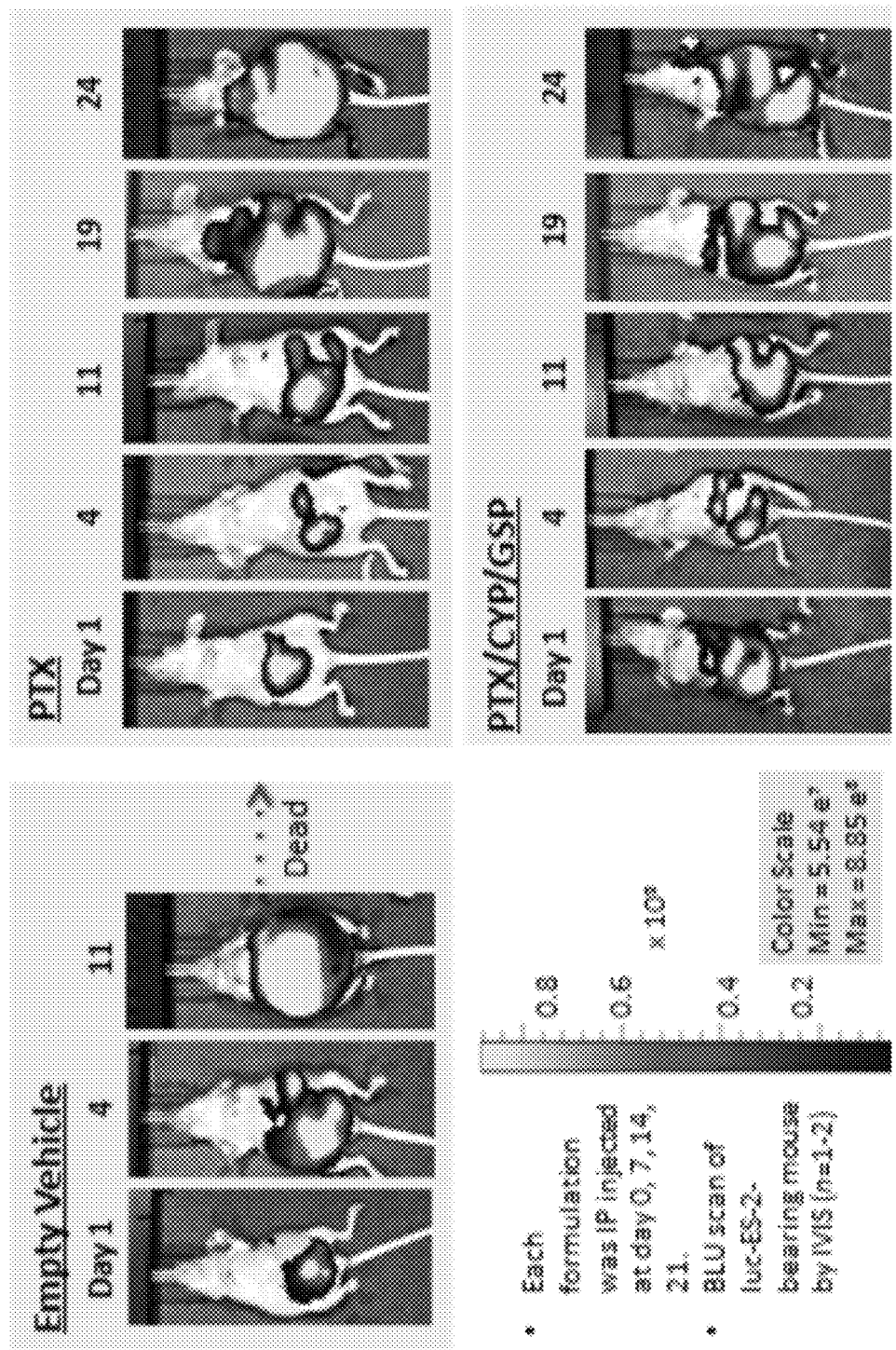
FIG. 8. Bioluminescence images (BLU) of luc-ES-2-bearing mouse illustrating animal whole-body bioluminescence (scanned by IVIS), and bioluminescence quantified by using IVIS software. The scans show the in vivo anticancer efficacy of the PTX/CYP/GSP three-drug micelle combination.
Figure 9:
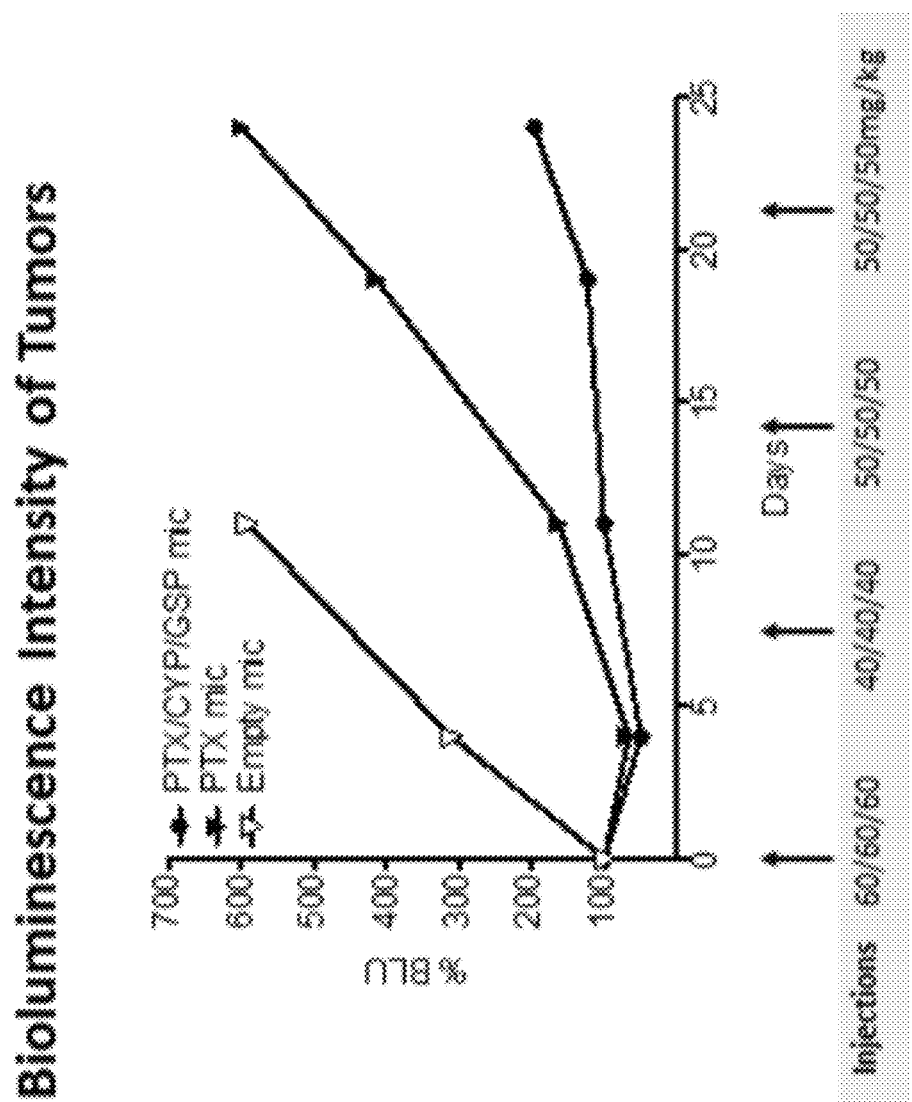
FIG. 9. Bioluminescence intensity of tumors shown in FIG. 8.

FIG. 8 illustrates the efficacy of the PTX/CYP/GSP three-drug combination incorporated into PEG-b-PCL micelles for the treatment of mice having ovarian cancer tumors, compared to a control and paclitaxel alone. The empty vehicle (control), PTX-incorporated $PEG_{5k}$-b-$PCL_{10k}$ micelles, and PTX/CYP/GSP-incorporated $PEG_{5k}$-b-$PCL_{10k}$ micelles were intravenously injected into luc-ES-2-bearing nude mice (6 days post cell inoculation), once a week, for four weeks. Luciferin substrate was IP injected 20 minutes before animal whole-body bioluminescence scanning (by IVIS) and bioluminescence was quantified by using IVIS software. The bioluminescence intensity of the tumors is further illustrated by FIG. 9.

The results in the figure clearly show that the three-drug combination in the micelle vehicle is far superior to the paclitaxel alone results. Accordingly, the three-drug micelle formulations can be effective treatments for the inhibition of ovarian cancer cells and the treatment of ovarian cancer tumors.

Example 3

Pharmaceutical Dosage Forms

The following formulations illustrate representative pharmaceutical dosage forms that may be used for the therapeutic administration of a micellar formulation described herein (hereinafter referred to as 'Composition X'):

| (i) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (ii) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (iii) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X' (dry weight of polymer-micelle film). Aerosol formulation (iii) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A micelle composition comprising an aqueous solvent system and drug-encapsulating micelles, wherein the micelles comprise a plurality of poloxamer polymers having an average molecular weight of about 1,000 g/mol to about 30,000 g/mol, the polymers form one or more micelles, the one or more micelles encapsulate a drug within their micelle structure, the drug is a gossypol compound that is not covalently bound to the polymer, and the diameter of the micelles is about 15 nm to about 150 nm.

2. The micelle composition of claim 1 wherein the drug is R-(−)gossypol or apogossypol.

3. The micelle composition of claim 2 wherein the polymer comprises poloxamer 188.

4. The micelle composition of claim 1 wherein the concentration of the gossypol compound in the composition is about 3 mg/mL to about 6 mg/mL.

5. The micelle composition of claim 4 wherein the one or more micelles comprise a second drug, or a second and third drug, encapsulated within the micelles.

6. The micelle composition of claim 5 wherein the concentration of each drug in the micelle composition is greater than about 3 mg/mL.

7. The micelle composition of claim 5 wherein the second or third drug is a paclitaxel compound, the second drug or third drug is a 17-AAG compound, or the second drug or third drug is a cyclopamine compound.

8. The micelle composition of claim 6 wherein the second or third drug is a paclitaxel compound, the second drug or third drug is a 17-AAG compound, or the second drug or third drug is a cyclopamine compound.

9. The micelle composition of claim 1 wherein micelles in the composition include within individual micelles the combination of gossypol, paclitaxel, and 17-AAG; or gossypol, paclitaxel, and cyclopamine.

10. The micelle composition of claim 1 wherein the amount of poloxamer polymers that form the micelles is less than the amount of poloxamer polymers required to reach the critical micelle concentration of the poloxamer polymer.

11. The micelle composition of claim 9 wherein the concentration of paclitaxel in the composition is about 4 mg/mL to about 7 mg/mL, the concentration of 17-AAG in the composition, if present, is about 1 mg/mL to about 7 mg/mL, or the concentration of cyclopamine in the composition, if present, is about 1 mg/mL to about 7 mg/mL.

12. The micelle composition of claim 10 wherein the micelles encapsulate a three drug combination, and the three drugs are gossypol, paclitaxel, and 17-AAG.

13. The micelle composition of claim 1 wherein the gossypol compound is (+/−)-gossypol; (−)-gossypol; (+)-gossypol; (+/−)-gossypolone; (−)-gossypolone; (+)-gossypolone; (+/−)-gossypol acetic acid; (−)-gossypol acetic acid; (+)-gossypol acetic acid; (+/−)-ethyl gossypol; (−)-ethyl gossypol; (+)-ethyl gossypol; (+/−)-hemigossypolone; (−)-hemigossypolone; (+)-hemigossypolone; (+/−)-apogossypol; (−)-apogossypol; (+)-apogossypol; (+/−)-apogossypol acetic acid; (−)-apogossypol acetic acid; (+)-apogossypol acetic acid; (+/−)-ethyl apogossypol; (−)-ethyl apogossypol; (+)-ethyl apogossypol; or a combination thereof.

14. A water soluble IV or IP formulation comprising gossypol loaded poloxamer 188 micelles and water, wherein the concentration of the gossypol in the formulation is at least about 3 mg/mL, and the formulation is free of organic solvents and surfactants.

15. The water soluble formulation of claim 14 further comprising paclitaxel and 17-AAG loaded within the poloxamer 188 micelles, wherein the formulation exerts anticancer activity against lung cancer cells.

16. The water soluble formulation of claim 14 further comprising paclitaxel and cyclopamine loaded in the poloxamer 188 micelles, wherein the formulation exerts superior anticancer activity against ovarian cancer cells compared to paclitaxel alone and the formulation breaks apart ovarian multicellular spheroids.

17. A method of inhibiting growth of cancer cells comprising contacting the cancer cells with an effective inhibitory amount of a composition as described in claim 1.

18. A method of inhibiting growth of cancer cells comprising contacting the cancer cells with an effective inhibitory amount of a composition as described in claim 9.

19. The method of claim 18 wherein the cancer cells comprise brain tumor cells, breast cancer cells, colon cancer cells, head and neck cancer cells, lung cancer cells, lymphoma cells, melanoma cells, neuroblastoma cells, ovarian cancer cells, pancreatic cancer cells, prostate cancer cells, or leukemia cells.

20. The micelle composition of claim 10 wherein the micelles encapsulate a three drug combination, and the three drugs are gossypol, paclitaxel, and cyclopamine.

21. The micelle composition of claim 10 wherein micelles in the composition include within individual micelles the combination of gossypol and paclitaxel; gossypol and 17-AAG; or gossypol and cyclopamine.

* * * * *